(12) United States Patent
Rabizadeh et al.

(10) Patent No.: US 11,810,672 B2
(45) Date of Patent: Nov. 7, 2023

(54) CANCER SCORE FOR ASSESSMENT AND RESPONSE PREDICTION FROM BIOLOGICAL FLUIDS

(71) Applicant: Nantomics, Culver City, CA (US)

(72) Inventors: Shahrooz Rabizadeh, Agoura Hills, CA (US); Patrick Soon-Shiong, Culver City, CA (US)

(73) Assignee: NantOmics, LLC, Culver City, CA (US)

( * ) Notice: Subject to any disclaimer, the term of this patent is extended or adjusted under 35 U.S.C. 154(b) by 338 days.

(21) Appl. No.: 16/754,088

(22) PCT Filed: Oct. 11, 2018

(86) PCT No.: PCT/US2018/055481
§ 371 (c)(1),
(2) Date: Apr. 6, 2020

(87) PCT Pub. No.: WO2019/075251
PCT Pub. Date: Apr. 18, 2019

(65) Prior Publication Data
US 2020/0335215 A1     Oct. 22, 2020

Related U.S. Application Data

(60) Provisional application No. 62/571,414, filed on Oct. 12, 2017.

(51) Int. Cl.
*G16H 50/20* (2018.01)
*G16H 50/30* (2018.01)
*G16H 50/70* (2018.01)
*G16H 20/40* (2018.01)
*G16H 70/60* (2018.01)
*G16H 10/40* (2018.01)
*G16H 10/60* (2018.01)
*G16H 20/10* (2018.01)
*G16B 20/20* (2019.01)
*G16B 20/10* (2019.01)
*G16B 25/10* (2019.01)

(52) U.S. Cl.
CPC ............ *G16H 50/20* (2018.01); *G16B 20/10* (2019.02); *G16B 20/20* (2019.02); *G16H 10/40* (2018.01); *G16H 10/60* (2018.01); *G16H 20/10* (2018.01); *G16H 20/40* (2018.01); *G16H 50/30* (2018.01); *G16H 50/70* (2018.01); *G16H 70/60* (2018.01); *G16B 25/10* (2019.02)

(58) Field of Classification Search
CPC ........ G16H 50/20; G16H 50/30; G16H 50/70; G16B 20/00; G16B 20/10; G16B 20/20; G16B 25/10
USPC .......................................................... 705/2
See application file for complete search history.

(56) References Cited

U.S. PATENT DOCUMENTS

| | | | |
|---|---|---|---|
| 9,422,592 B2 | 8/2016 | Morris et al. | |
| 2012/0059670 A1 | 3/2012 | Sanborn et al. | |
| 2012/0066001 A1 | 3/2012 | Sanborn et al. | |
| 2014/0329719 A1* | 11/2014 | Sulem | G16B 20/20 |
| | | | 702/19 |
| 2016/0032396 A1 | 2/2016 | Diehn et al. | |
| 2017/0211143 A1* | 7/2017 | Shendure | G16B 40/10 |
| 2017/0211153 A1 | 7/2017 | Kohli et al. | |
| 2018/0355423 A1* | 12/2018 | Yang | G16B 35/20 |
| 2019/0189241 A1* | 6/2019 | Tadmor | C12Q 1/6886 |

FOREIGN PATENT DOCUMENTS

| | | | |
|---|---|---|---|
| CA | 3 077 221 A1 | 4/2019 | |
| CN | 111213209 A | 5/2020 | |
| WO | 2013190089 A1 | 12/2013 | |
| WO | 2014194078 A1 | 12/2014 | |
| WO | 2016081947 A2 | 5/2016 | |
| WO | 2017091865 A1 | 6/2017 | |
| WO | 2019/075251 A2 | 4/2019 | |
| WO | 2019/075251 A3 | 7/2019 | |

OTHER PUBLICATIONS

International Preliminary Report on Patentability Chapter I received for PCT Application Serial No. PCT/US2018/055481 dated Apr. 23, 2020, 11 pages.
Jovelet et al., "Circulating cell-free tumor DNA (cfDNA) analysis of 50-genes by next-generation sequencing (NGS) in the prospective MOSCATO trial ", Clinical Cancer Research, 2016, 35 pages.
Kinoshita et al., "The Glasgow Prognostic Score, an Inflammation Based Prognostic Score, Predicts Survival in Patients With Hepatocellular Carcinoma", BMC Cancer, 2013, vol. 13, No. 52, pp. 1-11.
Kato et al., "A Comparison of Systemic Inflammation-Based Prognostic Scores in Patients on Regular Hemodialysis", Karger Open Access, 2013, vol. 3, 91-100.
Wikipedia, "Bloom-Richardson grading system", 2017, 2 pages.
Qian et al., "A clinical prognostic scoring system for resectable gastric cancer to predict survival and benefit from paclitaxel- or oxaliplatin-based adjuvant chemotherapy", Drug Design, Development and Therapy, 2016, vol. 10, pp. 241-258.

(Continued)

*Primary Examiner* — Jonathon A. Szumny
*Assistant Examiner* — Christopher B Wehrly
(74) *Attorney, Agent, or Firm* — Martin Fessenmaier; Umberg Zipser LLP

(57) ABSTRACT

Methods for analyzing omics data and using the omics data to determine prognosis of a cancer, to predict an outcome of a treatment, and/or to determine an effectiveness of a treatment are presented. In preferred methods, blood from a patient having a cancer or suspected to have a cancer is obtained and blood omics data for a plurality of cancer-related, inflammation-related, or DNA repair-related genes are obtained. A cancer score can be calculated based on the omics data, which then can be used to provide a cancer prognosis, a therapeutic recommendation, an effectiveness of a treatment.

18 Claims, No Drawings

(56) References Cited

OTHER PUBLICATIONS

Wikipedia, "Gleason grading system", 2017, 6 pages.
Pereira et al., "Personalized Circulating Tumor DNABiomarkers Dynamically Predict TreatmentResponse and Survival in Gynecologic-Cancers", Plos One, 2015, vol. 10, No. 12, pp. 1-13.
Jin et al., "Clinical utility of the modified Glasgowprognostic score in lung cancer: A metaanalysis", Plos One, 2017, vol. 12, No. 9, pp. 1-13.
Dawson et al., "Analysis of Circulating Tumor DNAto Monitor Metastatic Breast Cancer", The New England Journal of Medicine, 2013, vol. 368, No. 13, pp. 1199-1209.
Miura et al., "Glasgow prognostic score predicts prognosis for cancer patients in palliative settings: a subanalysis of the Japan-prognostic assessment tools validation (J-ProVal) study", Support Care Cancer, 2015, vol. 23, pp. 3149-3156.
Yi, X. et al., "The feasibility of using mutation detection in ctDNA to assess tumor dynamics", In. J. Cancer, Jun. 15, 2017 (Epub. Mar. 2, 2017), vol. 140, No. 12, pp. 2642-2647.
International Search Report with International Application No. PCT/US2018/055481 dated Oct. 11, 2018, 12 pages.

* cited by examiner

CANCER SCORE FOR ASSESSMENT AND RESPONSE PREDICTION FROM BIOLOGICAL FLUIDS This application claims priority to our US provisional application having the Ser. No. 62/571,414, filed Oct. 12, 2017, which is incorporated by reference in its entirety herein.

FIELD OF THE INVENTION

The field of the invention is profiling of omics data as they relate to cancer, especially as it relates to the generation of indicators for cancer prognosis, prediction of treatment outcomes, and/or effectiveness of cancer treatments.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer is a multifactorial disease where many diverse genetic and environmental factors interplay and contribute to the development and outcome of the disease. In addition, genetic and environmental factors often affect the patient's prognosis in various degrees such that individual patients may show different responses to the same therapeutic and/or prophylactic treatment. Such complexity and diversity render traditional prediction of prognosis, identification of optimal treatments, and prediction of likelihood of success of the treatments based on a single or few factors (e.g., serum level of inflammation-related proteins, etc.), often unreliable. Further, many traditional methods of examining such factors are invasive as they require tumor biopsy samples for histology of tumor cells and tissues.

More recently, DNA or RNA populations present in the peripheral blood have drawn attention for analyzing genetic abnormalities associated with the cancer status. For example, U.S. Pat. No. 9,422,592 discloses the measurement of cell free RNA (cfRNA) of formulpeptide receptor gene (FPR1) and its association with the patient's risk for having lung cancer or non-small cell lung cancer (NSCLC). Yet, such studies are limited to a few numbers of genes, which are typically weighed equally in determining the cancer status. As multiple factors affect to various degrees prognosis of most cancers, oversimplification may cause inaccurate prognosis and/or prediction of treatment outcome.

Thus, even though some examples of using cell free nucleic acid in determining cancer status are known, differentially weighed, multi-factor approaches in determining cancer status using cell free nucleic acid are largely unexplored. Thus, there remains a need for improved methods of analyzing omics data of cell free nucleic acids in determining status, prognosis of a cancer as well as likelihood of treatment outcome or effectiveness of the treatment.

SUMMARY OF THE INVENTION

The inventive subject matter is directed to methods of using various omics data of cell free nucleic acids to calculate a composite cancer score that can be used to determine the status, prognosis of a cancer as well as likelihood of treatment outcome and/or effectiveness of current treatments. Thus, one aspect of the subject matter includes a method of analyzing omics data. In this method, blood is obtained from a patient having or suspected to have a cancer. From the blood, omics data for a plurality of cancer-related genes are obtained. Most preferably, the omics data include at least one of DNA sequence data, RNA sequence data, and RNA expression level data. From the omics data, a composite score is calculated which can then be associated with at least one of a health status, an omics error status, a cancer prognosis, a therapeutic recommendation, and an effectiveness of a treatment.

In some embodiments, the DNA sequence data v selected from the group consisting of mutation data, copy number data duplication, loss of heterozygosity data, and epigenetic status. Optionally, the DNA sequence data is obtained from circulating free DNA. In other embodiments, the RNA sequence data is selected from the group consisting of mRNA sequence data and splice variant data, and/or the RNA expression level data is selected from the group consisting of a quantity of RNA transcript and a quantity of a small noncoding RNA. Optionally, the RNA sequence data is obtained from the group consisting of circulating tumor RNA and circulating free RNA.

Typically, the plurality of cancer-related genes comprises at least one of a cancer-related gene, a cancer-specific gene, a DNA-repair gene, a neoepitope, and a gene not associated with a disease. Preferably, the neoepitope is tumor-specific and patient-specific. In some embodiments, the plurality of cancer-related genes includes a cancer-specific gene, and the score is calculated based on a presence or an absence of a mutation in the cancer-specific gene. In such embodiments, it is preferred that the presence of the mutation in the cancer-specific gene weighs more than the presence of the mutation in the cancer-related genes other than the cancer-specific gene. In other embodiments, the score is calculated based on a type of a splice variant of the cancer gene or a ratio between or among a plurality of splice variants of the cancer gene.

In some embodiments, the method further comprises a step of comparing the score with a threshold value to thereby determine the therapeutic recommendation. In such embodiments, it is preferred that the therapeutic recommendation is a prophylactic treatment if the score is below the threshold value. Alternatively and/or additionally, the method further comprises a step of comparing the omics error status with a threshold value to thereby determine a risk score.

In another aspect of the inventive subject matter, the inventors contemplate a method of determining prognosis of a cancer of a patient. In this method, blood is obtained from a patient having or suspected to have a cancer. From the blood, omics data for a plurality of cancer genes are obtained. Preferably, the omics data include at least one of DNA sequence data, RNA sequence data, and RNA expression level data. From the omics data, a cancer prognosis score is calculated, and the prognosis of the cancer is provided based on the cancer prognosis score. IN some embodiments, the prognosis comprises a progress of metastasis.

In some embodiments, the DNA sequence data v selected from the group consisting of mutation data, copy number data duplication, loss of heterozygosity data, and epigenetic status. Optionally, the DNA sequence data is obtained from circulating free DNA. In other embodiments, the RNA sequence data is selected from the group consisting of mRNA sequence data and splice variant data, and/or the RNA expression level data is selected from the group consisting of a quantity of RNA transcript and a quantity of a small noncoding RNA. Optionally, the RNA sequence data is obtained from the group consisting of circulating tumor RNA and circulating free RNA.

Typically, the plurality of cancer-related genes comprises at least one of a cancer-related gene, a cancer-specific gene, a DNA-repair gene, a neoepitope, and a gene not associated with a disease. Preferably, the neoepitope is tumor-specific and patient-specific. In some embodiments, the plurality of cancer-related genes includes a cancer-specific gene, and the score is calculated based on a presence or an absence of a mutation in the cancer-specific gene. In other embodiments, the score is calculated based on a type of a splice variant of the cancer gene or a ratio among or between a plurality of splice variants of the cancer gene.

In some embodiments, the omics data is a plurality of sets of omics data obtained at a different time points during a time period, and the prognosis is provided based on a plurality of scores from the plurality of sets of omics data. In such embodiments, it is preferred that the prognosis is represented by a change of a plurality of scores during the time period, wherein the change is over a predetermined threshold value.

Still another aspect of inventive subject matter is directed towards a method of predicting an outcome of a treatment for a cancer patient. In this method, blood is obtained from a patient having a cancer. From the blood, omics data for a plurality of cancer genes are obtained. Preferably, the omics data include at least one of DNA sequence data, RNA sequence data, and RNA expression level data. From the omics data, a cancer gene score is calculated, and a predicted outcome of the treatment is provided based on the cancer prognosis score. Preferably, the predicted outcome is determined by comparing the cancer gene score with a predetermined threshold value.

In some embodiments, the treatment is a drug, and at least one of the plurality of cancer gene is a predicted target of the drug. In other embodiments, the treatment is an immune therapy, and at least one of the plurality of cancer gene is a receptor of an immune cell or a ligand of the receptor. In still other embodiments, the treatment is a surgery or a radiation therapy, and at least one of the plurality of cancer gene is a neoepitope that is tumor-specific and patient-specific.

In some embodiments, the DNA sequence data v selected from the group consisting of mutation data, copy number data duplication, loss of heterozygosity data, and epigenetic status. Optionally, the DNA sequence data is obtained from circulating free DNA. In other embodiments, the RNA sequence data is selected from the group consisting of mRNA sequence data and splice variant data, and/or the RNA expression level data is selected from the group consisting of a quantity of RNA transcript and a quantity of a small noncoding RNA. Optionally, the RNA sequence data is obtained from the group consisting of circulating tumor RNA and circulating free RNA.

Typically, the plurality of cancer-related genes comprises at least one of a cancer-related gene, a cancer-specific gene, a DNA-repair gene, a neoepitope, and a gene not associated with a disease. Preferably, the neoepitope is tumor-specific and patient-specific. In some embodiments, the plurality of cancer-related genes includes a cancer-specific gene, and the score is calculated based on a presence or an absence of a mutation in the cancer-specific gene. In other embodiments, the score is calculated based on a type of a splice variant of the cancer gene or a ratio between a plurality of splice variants of the cancer gene.

In still another aspect of the inventive subject matter, the inventors contemplate a method of evaluating an effectiveness of a treatment for a cancer patient. In this method, blood is obtained from a patient having a cancer. From the blood, omics data for a plurality of cancer genes are obtained before and after the treatment. Preferably, the omics data include at least one of DNA sequence data, RNA sequence data, and RNA expression level data. From the omics data, at least two cancer gene scores corresponding to the omics data before and after the treatment, respectively, are generated, and the effectiveness of the treatment is provided based on the comparison of the at least two cancer gene scores. In some embodiments, the effectiveness of the treatment can be determined by a difference between the cancer gene score before and after the treatment. In such embodiments, it is preferred that the treatment is determined effective when the difference is higher than a predetermined threshold value.

In some embodiments, the treatment is a drug, and at least one of the plurality of cancer gene is a predicted target of the drug. In other embodiments, the treatment is an immune therapy, and at least one of the plurality of cancer gene is a receptor of an immune cell or a ligand of the receptor. In still other embodiments, the treatment is a surgery or a radiation therapy, and at least one of the plurality of cancer gene is a neoepitope that is tumor-specific and patient-specific.

In some embodiments, the DNA sequence data v selected from the group consisting of mutation data, copy number data duplication, loss of heterozygosity data, and epigenetic status. Optionally, the DNA sequence data is obtained from circulating free DNA. In other embodiments, the RNA sequence data is selected from the group consisting of mRNA sequence data and splice variant data, and/or the RNA expression level data is selected from the group consisting of a quantity of RNA transcript and a quantity of a small noncoding RNA. Optionally, the RNA sequence data is obtained from the group consisting of circulating tumor RNA and circulating free RNA.

Typically, the plurality of cancer-related genes comprises at least one of a cancer-related gene, a cancer-specific gene, a DNA-repair gene, a neoepitope, and a gene not associated with a disease. Preferably, the neoepitope is tumor-specific and patient-specific. In some embodiments, the plurality of cancer-related genes includes a cancer-specific gene, and the score is calculated based on a presence or an absence of a mutation in the cancer-specific gene. In other embodiments, the score is calculated based on a type of a splice variant of the cancer gene or a ratio between a plurality of splice variants of the cancer gene.

Various objects, features, aspects and advantages of the inventive subject matter will become more apparent from the following detailed description of preferred embodiments.

DETAILED DESCRIPTION

The inventors discovered that the status and/or prognosis of a cancer can be more reliably determined in a less invasive and quick manner using a compound score that is generated based on multiple factors associated with the cancer. The inventors also discovered that the compound score can be used to reliably predict a likelihood of outcome of a cancer treatment, and further, effectiveness of a particular cancer treatment. Viewed from a different perspective, the inventors discovered that a compound score can be generated from the patient's omics data obtained from nucleic acids in the patient's blood. Typically the omics data include omics data of various cancer-related genes, which can be differentially weighed based on the type and timing of the sampling. The compound score can be a reliable indicator to determine cancer status and/or prognosis of a cancer, a likelihood of outcome of a cancer treatment. Further, the compound scores generated based on omics data obtained before and after a cancer treatment can be compared to determine the effectiveness of a cancer treatment.

As used herein, the term "tumor" refers to, and is interchangeably used with one or more cancer cells, cancer tissues, malignant tumor cells, or malignant tumor tissue, that can be placed or found in one or more anatomical locations in a human body.

It should be noted that the term "patient" as used herein includes both individuals that are diagnosed with a condition (e.g., cancer) as well as individuals undergoing examination and/or testing for the purpose of detecting or identifying a condition. Thus, a patient having a tumor refers to both individuals that are diagnosed with a cancer as well as individuals that are suspected to have a cancer.

As used herein, the term "provide" or "providing" refers to and includes any acts of manufacturing, generating, placing, enabling to use, transferring, or making ready to use.

Cell-Free DNA/RNA

The inventors contemplate that tumor cells and/or some immune cells interacting or surrounding the tumor cells release cell free DNA/RNA to the patient's bodily fluid, and thus may increase the quantity of the specific cell free DNA/RNA in the patient's bodily fluid as compared to a healthy individual. As used herein, the patient's bodily fluid includes, but is not limited to, blood, serum, plasma, mucus, cerebrospinal fluid, ascites fluid, saliva, and urine of the patient. Alternatively, it should be noted that various other bodily fluids are also deemed appropriate so long as cell free DNA/RNA is present in such fluids. The patient's bodily fluid may be fresh or preserved/frozen. Appropriate fluids include saliva, ascites fluid, spinal fluid, urine, etc., which may be fresh or preserved/frozen.

The cell free RNA may include any types of DNA/RNA that are circulating in the bodily fluid of a person without being enclosed in a cell body or a nucleus. Most typically, the source of the cell free DNA/RNA is the tumor cells. However, it is also contemplated that the source of the cell free DNA/RNA is an immune cell (e.g., NK cells, T cells, macrophages, etc.). Thus, the cell free DNA/RNA can be circulating tumor DNA/RNA (ctDNA/RNA) and/or circulating free DNA/RNA (cf DNA/RNA, circulating nucleic acids that do not derive from a tumor). While not wishing to be bound by a particular theory, it is contemplated that release of cell free DNA/RNA originating from a tumor cell can be increased when the tumor cell interacts with an immune cell or when the tumor cells undergo cell death (e.g., necrosis, apoptosis, autophagy, etc.). Thus, in some embodiments, the cell free DNA/RNA may be enclosed in a vesicular structure (e.g., via exosomal release of cytoplasmic substances) so that it can be protected from nuclease (e.g., RNAase) activity in some type of bodily fluid. Yet, it is also contemplated that in other aspects, the cell free DNA/RNA is a naked DNA/RNA without being enclosed in any membranous structure, but may be in a stable form by itself or be stabilized via interaction with one or more non-nucleotide molecules (e.g., any RNA binding proteins, etc.).

It is contemplated that the cell free DNA/RNA can be any type of DNA/RNA which can be released from either cancer cells or immune cell. Thus, the cell free DNA may include any whole or fragmented genomic DNA, or mitochondrial DNA, and the cell free RNA may include mRNA, tRNA, microRNA, small interfering RNA, long non-coding RNA (lncRNA). Most typically, the cell free DNA is a fragmented DNA typically with a length of at least 50 base pair (bp), 100 base pair (bp), 200 bp, 500 bp, or 1 kbp. Also, it is contemplated that the cell free RNA is a full length or a fragment of mRNA (e.g., at least 70% of full-length, at least 50% of full length, at least 30% of full length, etc.). While cell free DNA/RNA may include any type of DNA/RNA encoding any cellular, extracellular proteins or non-protein elements, it is preferred that at least some of cell free DNA/RNA encodes one or more cancer-related proteins, or inflammation-related proteins. For example, the cell free DNA/mRNA may be full-length or fragments of (or derived from the) cancer related genes including, but not limited to ABL1, ABL2, ACTB, ACVR1B, AKT1, AKT2, AKT3, ALK, AMER11, APC, AR, ARAF, ARFRP1, ARID1A, ARID1B, ASXL1, ATF1, ATM, ATR, ATRX, AURKA, AURKB, AXIN1, AXL, BAP1, BARD1, BCL2, BCL2L1, BCL2L2, BCL6, BCOR, BCORL1, BLM, BMPR1A, BRAF, BRCA1, BRCA2, BRD4, BRIP1, BTG1, BTK, EMSY, CARD11, CBFB, CBL, CCND1, CCND2, CCND3, CCNE1, CD274, CD79A, CD79B, CDC73, CDH1, CDK12, CDK4, CDK6, CDK8, CDKN1A, CDKN1B, CDKN2A, CDKN2B, CDKN2C, CEA, CEBPA, CHD2, CHD4, CHEK1, CHEK2, CIC, CREBBP, CRKL, CRLF2, CSF1R, CTCF, CTLA4, CTNNA1, CTNNB1, CUL3, CYLD, DAXX, DDR2, DEPTOR, DICER1, DNMT3A, DOT1L, EGFR, EP300, EPCAM, EPHA3, EPHA5, EPHA7, EPHB1, ERBB2, ERBB3, ERBB4, EREG, ERG, ERRFI1, ESR1, EWSR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR1, FGFR2, FGFR3, FGFR4, FH, FLCN, FLI1, FLT1, FLT3, FLT4, FOLH1, FOXL2, FOXP1, FRS2, FUBP1, GABRA6, GATA1, GATA2, GATA3, GATA4, GATA6, GID4, GLI1, GNA11, GNA13, GNAQ, GNAS, GPR124, GRIN2A, GRM3, GSK3B, H3F3A, HAVCR2, HGF, HMGB1, HMGB2, HMGB3, HNF1A, HRAS, HSD3B1, HSP90AA1, IDH1, IDH2, IDO, IGF1R, IGF2, IKBKE, IKZF1, IL7R, INHBA, INPP4B, IRF2, IRF4, IRS2, JAK1, JAK2, JAK3, JUN, MYST3, KDM5A, KDM5C, KDM6A, KDR, KEAP, KEL, KIT, KLHL6, KLK3, MLL, MLL2, MLL3, KRAS, LAG3, LMO1, LRP1B, LYN, LZTR1, MAGI2, MAP2K1, MAP2K2, MAP2K4, MAP3K1, MCL1, MDM2, MDM4, MED12, MEF2B, MEN1, MET, MITF, MLH1, MPL, MRE11A, MSH2, MSH6, MTOR, MUC1, MUTYH, MYC, MYCL, MYCN, MYD88, MYH, NF1, NF2, NFE2L2, NFKB1A, NKX2-1, NOTCH1, NOTCH2, NOTCH3, NPM1, NRAS, NSD1, NTRK1, NTRK2, NTRK3, NUP93, PAK3, PALB2, PARK2, PAX3, PAX, PBRM1, PDGFRA, PDCD1, PDCD1LG2, PDGFRB, PDK1, PGR, PIK3C2B, PIK3CA, PIK3CB, PIK3CG, PIK3R1, PIK3R2, PLCG2, PMS2, POLD1, POLE, PPP2R1A, PREX2, PRKAR1A, PRKC1, PRKDC, PRSS8, PTCH1, PTEN, PTPN11, QK1, RAC1, RAD50, RAD51, RAF1, RANBP1, RARA, RB1, RBM10, RET, RICTOR, RIT1, RNF43, ROS1, RPTOR, RUNX1, RUNX1T1, SDHA, SDHB, SDHC, SDHD, SETD2, SF3B1, SLIT2, SMAD2, SMAD3, SMAD4, SMARCA4, SMARCB1, SMO, SNCAIP, SOCS1, SOX10, SOX2, SOX9, SPEN, SPOP, SPTA1, SRC, STAG2, STAT3, STAT4, STK11, SUFU, SYK, T (BRACHYURY), TAF1, TBX3, TERC, TERT, TET2, TGFRB2, TNFAIP3, TNFRSF14, TOP1, TOP2A, TP53, TSC1, TSC2, TSHR, U2AF1, VEGFA, VHL, WISP3, WT1, XPO1, ZBTB2, ZNF217, ZNF703, CD26, CD49F, CD44, CD49F, CD13, CD15, CD29, CD151, CD138, CD166, CD133, CD45, CD90, CD24, CD44, CD38, CD47, CD96, CD 45, CD90, ABCB5, ABCG2, ALCAM, ALPHA-FETOPROTEIN, DLL1, DLL3, DLL4, ENDOGLIN, GJA1, OVASTACIN, AMACR, NESTIN, STRO-1, MICL, ALDH, BMI-1, GLI-2, CXCR1, CXCR2, CX3CR1, CX3CL1, CXCR4, PON1, TROP1, LGR5, MSI-1, C-MAF, TNFRSF7, TNFRSF16, SOX2, PODOPLANIN, L1CAM, HIF-2 ALPHA, TFRC, ERCC1, TUBB3, TOP1, TOP2A, TOP2B, ENOX2, TYMP, TYMS, FOLR1, GPNMB, PAPPA, GART, EBNA1, EBNA2, LMP1, BAGE, BAGE2, BCMA, C10ORF54, CD4, CD8, CD19, CD20, CD25, CD30, CD33, CD80, CD86, CD123, CD276, CCL1, CCL2, CCL3, CCL4, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CCR1, CCR2, CCR3, CCR4, CCR5, CCR6, CCR7, CCR8, CCR9, CCR10, CXCL1, CXCL2, CXCL3, CXCL5, CXCL6, CXCL9, CXCL10, CXCL11, CXCL12, CXCL13, CXCL14, CXCL16, CXCL17, CXCR3, CXCR5, CXCR6, CTAG1B, CTAG2, CTAG1, CTAG4, CTAG5, CTAG6, CTAG9, CAGE1, GAGE1, GAGE2A, GAGE2B, GAGE2C, GAGE2D, GAGE2E, GAGE4, GAGE10, GAGE12D, GAGE12F, GAGE12J, GAGE13, HHLA2, ICOSLG, LAG1, MAGEA10, MAGEA12, MAGEA1, MAGEA2, MAGEA3, MAGEA4, MAGEA4, MAGEA5, MAGEA6, MAGEA7, MAGEA8, MAGEA9, MAGEB1, MAGEB2, MAGEB3, MAGEB4, MAGEB6, MAGEB10, MAGEB16, MAGEB18, MAGEC1, MAGEC2, MAGEC3, MAGED1, MAGED2, MAGED4, MAGED4B, MAGEE1, MAGEE2, MAGEF1, MAGEH1, MAGEL2, NCR3LG1, SLAMF7, SPAG1, SPAG4, SPAG5, SPAG6, SPAG7, SPAG8, SPAG9, SPAG11A, SPAG11B, SPAG16, SPAG17, VTCN1, XAGE1D, XAGE2, XAGE3, XAGE5, XCL1, XCL2, and XCR1. Of course, it should be appreciated that the above genes may be wild type or mutated versions, including missense or nonsense mutations, insertions, deletions, fusions, and/or translocations, all of which may or may not cause formation of full-length mRNA when transcribed.

For another example, some cell free DNAs/mRNAs are fragments of or those encoding a full length or a fragment of inflammation-related proteins, including, but not limited to, HMGB1, HMGB2, HMGB3, MUC1, VWF, MMP, CRP, PBEF1, TNF-α, TGF-β, PDGFA, IL-1, IL-2, IL-3, IL-4, IL-5, IL-6, IL-7, IL-8, IL-9, IL-10, IL-12, IL-13, IL-15, IL-17, Eotaxin, FGF, G-CSF, GM-CSF, IFN-γ, IP-10, MCP-1, PDGF, and hTERT, and in yet another example, the cell free mRNA encoded a full length or a fragment of HMGB1.

For still another example, some cell free DNAs/mRNAs are fragments of or those encoding a full length or a fragment of DNA repair-related proteins or RNA repair-related proteins. Table 1 provides an exemplary collection of predominant RNA repair genes and their associated repair pathways contemplated herein, but it should be recognized that numerous other genes associated with DNA repair and repair pathways are also expressly contemplated herein, and Tables 2 and 3 illustrate further exemplary genes for analysis and their associated function in DNA repair.

TABLE 1

| Repair mechanism | Predominant DNA Repair genes |
| --- | --- |
| Base excision repair (BER) | DNA glycosylase, APE1, XRCC1, PNKP, Tdp1, APTX, DNA polymerase β, FEN1, DNA polymerase δ or ε, PCNA-RFC, PARP |
| Mismatch repair (MMR) | MutSα (MSH2-MSH6), Mutsβ (MSH2-MSH3), MutLα (MLH1-PMS2), MutLβ (MLH1-PMS2), MutLγ (MLH1-MLH3), Exo1, PCNA-RFC |
| Nucleotide excision repair (NER) | XPC-Rad23B-CEN2, UV-DDB (DDB1-XPE), CSA, CSB, TFIIH, XPB, XPD, XPA, RPA, XPG, ERCC1- XPF, DNA polymerase δ or ε |
| Homologous recombination (HR) | Mre11-Rad50-Nbs1, CtIP, RPA, Rad51, Rad52, BRCA1, BRCA2, Exo1, BLM-TopIIIα, GEN1-Yen1, Slx1-Slx4, Mus81/Eme1 |
| Non-homologous end-joining (NHEJ) | Ku70-Ku80, DNA-PKc, XRCC4-DNA ligase IV, XLF |

TABLE 2

| Gene name (synonyms) | Activity | Accession number |
| --- | --- | --- |
| Base excision repair (BER) | | |
| | DNA glycosylases: major altered base released | |
| UNG | U excision | NM_003362 |
| SMUG1 | U excision | NM_014311 |
| MBD4 | U or T opposite G at CpG sequences | NM_003925 |
| TDG | U, T or ethenoC opposite G | NM_003211 |
| OGG1 | 8-oxoG opposite C | NM_002542 |
| MYH | A opposite 8-oxoG | NM_012222 |
| NTH1 | Ring-saturated or fragmented pyrimidines | NM_002528 |
| MPG | 3-meA, ethenoA, hypoxanthine | NM_002434 |
| | Other BER factors | |
| APE1 (HAP1, APEX, REF1) | AP endonuclease | NM_001641 |
| APE2 (APEXL2) | AP endonuclease | NM_014481 |
| LIG3 | Main ligation function | NM_013975 |
| XRCC1 | Main ligation function | NM_006297 |

TABLE 2-continued

| Gene name (synonyms) | Activity | Accession number |
|---|---|---|
| *Poly(ADP-ribose) polymerase (PARP) enzymes* | | |
| ADPRT | Protects strand interruptions | NM_001618 |
| ADPRTL2 | PARP-like enzyme | NM_005485 |
| ADPRTL3 | PARP-like enzyme | AF085734 |
| *Direct reversal of damage* | | |
| MGMT | O6-meG alkyltransferase | NM_002412 |
| *Mismatch excision repair (MMR)* | | |
| MSH2 | Mismatch and loop recognition | NM_000251 |
| MSH3 | Mismatch and loop recognition | NM_002439 |
| MSH6 | Mismatch recognition | NM_000179 |
| MSH4 | MutS homolog specialized for meiosis | NM_002440 |
| MSH5 | MutS homolog specialized for meiosis | NM_002441 |
| PMS1 | Mitochondrial MutL homolog | NM_000534 |
| MLH1 | MutL homolog | NM_000249 |
| PMS2 | MutL homolog | NM_000535 |
| MLH3 | MutL homolog of unknown function | NM_014381 |
| PMS2L3 | MutL homolog of unknown function | D38437 |
| PMS2L4 | MutL homolog of unknown function | D38438 |
| *Nucleotide excision repair (NER)* | | |
| XPC | Binds damaged DNA as complex | NM_004628 |
| RAD23B (HR23B) | Binds damaged DNA as complex | NM_002874 |
| CETN2 | Binds damaged DNA as complex | NM_004344 |
| RAD23A (HR23A) | Substitutes for HR23B | NM_005053 |
| χPA | Binds damaged DNA in preincisioncomplex | NM_000380 |
| RPA1 | Binds DNA in preincision complex | NM_002945 |
| RPA2 | Binds DNA in preincision complex | NM_002946 |
| RPA3 | Binds DNA in preincision complex | NM_002947 |
| TFIIH | Catalyzes unwinding in preincisioncomplex | |
| XPB (ERCC3) | 3' to 5' DNA helicase | NM_000122 |
| XPD (ERCC2) | 5' to 3' DNA helicase | X52221 |
| GTF2H1 | Core TFIIH subunit p62 | NM_005316 |
| GTF2H2 | Core TFIIH subunit p44 | NM_001515 |
| GTF2H3 | Core TFIIH subunit p34 | NM_001516 |
| GTF2H4 | Core TFIIH subunit p52 | NM_001517 |
| CDK7 | Kinase subunit of TFIIH | NM_001799 |
| CCNH | Kinase subunit of TFIIH | NM_001239 |
| MNAT1 | Kinase subunit of TFIIH | NM_002431 |
| XPG (ERCC5) | 3' incision | NM_000123 |
| ERCC1 | 5' incision subunit | NM_001983 |
| XPF (ERCC4) | 5' incision subunit | NM_005236 |
| LIG1 | DNA joining | NM_000234 |
| *NER-related* | | |
| CSA (CKN1) | Cockayne syndrome; needed for transcription-coupled NER | NM_000082 |
| CSB (ERCC6) | Cockayne syndrome; needed for transcription-coupled NER | NM_000124 |
| XAB2 (HCNP) | Cockayne syndrome; needed for transcription-coupled NER | NM_020196 |
| DDB1 | Complex defective in XP group E | NM_001923 |
| DDB2 | Mutated in XP group E | NM_000107 |
| MMS19 | Transcription and NER | AW852889 |
| *Homologous recombination* | | |
| RAD51 | Homologous pairing | NM_002875 |
| RAD51L1 (RAD51B) | Rad51 homolog | U84138 |
| RAD51C | Rad51 homolog | NM_002876 |
| RAD51L3 (RAD51D) | Rad51 homolog | NM_002878 |
| DMC1 | Rad51 homolog, meiosis | NM_007068 |
| XRCC2 | DNA break and cross-link repair | NM_005431 |
| XRCC3 | DNA break and cross-link repair | NM_005432 |
| RAD52 | Accessory factor for recombination | NM_002879 |
| RAD54L | Accessory factor for recombination | NM_003579 |
| RAD54B | Accessory factor for recombination | NM_012415 |
| BRCA1 | Accessory factor for transcription and recombination | NM_007295 |
| BRCA2 | Cooperation with RAD51, essential function | NM_000059 |

TABLE 2-continued

| Gene name (synonyms) | Activity | Accession number |
|---|---|---|
| RAD50 | ATPase in complex with MRE11A, NBS1 | NM_005732 |
| MRE11A | 3' exonuclease | NM_005590 |
| NBS1 | Mutated in Nijmegen breakage syndrome | NM_002485 |
| Nonhomologous end-joining | | |
| Ku70 (G22P1) | DNA end binding | NM_001469 |
| Ku80 (XRCC5) | DNA end binding | M30938 |
| PRKDC | DNA-dependent protein kinase catalytic subunit | NM_006904 |
| LIG4 | Nonhomologous end-joining | NM_002312 |
| XRCC4 | Nonhomologous end-joining | NM_003401 |
| Sanitization of nucleotide pools | | |
| MTH1 (NUDT1) | 8-oxoGTPase | NM_002452 |
| DUT | dUTPase | NM_001948 |
| DNA polymerases (catalytic subunits) | | |
| POLB | BER in nuclear DNA | NM_002690 |
| POLG | BER in mitochondrial DNA | NM_002693 |
| POLD1 | NER and MMR | NM_002691 |
| POLE1 | NER and MMR | NM_006231 |
| PCNA | Sliding clamp for pol delta and pol epsilon | NM_002592 |
| REV3L (POLZ) | DNA pol zeta catalytic subunit, essential function | NM_002912 |
| REV7 (MAD2L2) | DNA pol zeta subunit | NM_006341 |
| REV1 | dCMP transferase | NM_016316 |
| POLH | XP variant | NM_006502 |
| POLI (RAD30B) | Lesion bypass | NM_007195 |
| POLQ | DNA cross-link repair | NM_006596 |
| DINB1 (POLK) | Lesion bypass | NM_016218 |
| POLL | Meiotic function | NM_013274 |
| POLM | Presumed specialized lymphoid function | NM_013284 |
| TRF4-1 | Sister-chromatid cohesion | AF089896 |
| TRF4-2 | Sister-chromatid cohesion | AF089897 |
| Editing and processing nucleases | | |
| FEN1 (DNase IV) | 5' nuclease | NM_004111 |
| TREX1 (DNase III) | 3' exonuclease | NM_007248 |
| TREX2 | 3' exonuclease | NM_007205 |
| EX01 (HEX1) | 5' exonuclease | NM_003686 |
| SPO11 | endonuclease | NM_012444 |
| Rad6 pathway | | |
| UBE2A (RAD6A) | Ubiquitin-conjugating enzyme | NM_003336 |
| UBE2B (RAD6B) | Ubiquitin-conjugating enzyme | NM_003337 |
| RAD18 | Assists repair or replication of damaged DNA | AB035274 |
| UBE2VE (MMS2) | Ubiquitin-conjugating complex | AF049140 |
| UBE2N (UBC13, BTG1) | Ubiquitin-conjugating complex | NM_003348 |
| Genes defective in diseases associated with sensitivity to DNA damaging agents | | |
| BLM | Bloom syndrome helicase | NM_000057 |
| WRN | Werner syndrome helicase/3'-exonuclease | NM_000553 |
| RECQL4 | Rothmund-Thompson syndrome | NM_004260 |
| ATM | Ataxia telangiectasia | NM_000051 |
| Fanconi anemia | | |
| FANCA | Involved in tolerance or repair of DNA cross-links | NM_000135 |
| FANCB | Involved in tolerance or repair of DNA cross-links | N/A |
| FANCC | Involved in tolerance or repair of DNA cross-links | NM_000136 |
| FANCD | Involved in tolerance or repair of DNA cross-links | N/A |
| FANCE | Involved in tolerance or repair of DNA cross-links | NM_021922 |
| FANCF | Involved in tolerance or repair of DNA cross-links | AF181994 |
| FANCG (XRCC9) | Involved in tolerance or repair of DNA cross-links | NM_004629 |

TABLE 2-continued

| Gene name (synonyms) | Activity | Accession number |
|---|---|---|
| Other identified genes with a suspected DNA repair function | | |
| SNM1 (PSO2) | DNA cross-link repair | D42045 |
| SNM1B | Related to SNM1 | AL137856 |
| SNM1C | Related to SNM1 | AA315885 |
| RPA4 | Similar to RPA2 | NM_013347 |
| ABH (ALKB) | Resistance to alkylation damage | X91992 |
| PNKP | Converts some DNA breaks to ligatable ends | NM_007254 |
| Other conserved DNA damage response genes | | |
| ATR | ATM- and PI-3K-like essential kinase | NM_001184 |
| RAD1 (S. pombe) homolog | PCNA-like DNA damage sensor | NM_002853 |
| RAD9 (S. pombe) homolog | PCNA-like DNA damage sensor | NM_004584 |
| HUS1 (S. pombe) homolog | PCNA-like DNA damage sensor | NM_004507 |
| RAD17 (RAD24) | RFC-like DNA damage sensor | NM_002873 |
| TP53BP1 | BRCT protein | NM_005657 |
| CHEK1 | Effector kinase | NM_001274 |
| CHK2 (Rad53) | Effector kinase | NM_007194 |

TABLE 3

| Gene Name | Gene Title | Biological Activity |
|---|---|---|
| RFC2 | replication factor C (activator 1) 2, 40 kDa | DNA replication |
| XRCC6 | X-ray repair complementing defective repair in Chinese hamster cells 6 (Ku autoantigen, 70 kDa) | DNA ligation /// DNA repair /// double-strand break repair via nonhomologous end-joining /// DNA recombination /// positive regulation of transcription, DNA-dependent /// double-strand break repair via nonhomologous end-joining /// response to DNA damage stimulus /// DNA recombination |
| APOBEC | apolipoprotein B mRNA editing enzyme, catalytic polypeptide-like | For all of APOBEC1, APOBEC2, APOBEC3A-H, and APOBEC4, cytidine deaminases. |
| POLD2 | polymerase (DNA directed), delta 2, regulatory subunit 50 kDa | DNA replication /// DNA replication |
| PCNA | proliferating cell nuclear antigen | regulation of progression through cell cycle /// DNA replication /// regulation of DNA replication /// DNA repair /// cell proliferation /// phosphoinositide-mediated signaling /// DNA replication |
| RPA1 | replication protein A1, 70 kDa | DNA-dependent DNA replication /// DNA repair /// DNA recombination /// DNA replication |
| RPA1 | replication protein A1, 70 kDa | DNA-dependent DNA replication /// DNA repair /// DNA recombination /// DNA replication |
| RPA2 | replication protein A2, 32 kDa | DNA replication /// DNA-dependent DNA replication |
| ERCC3 | excision repair cross-complementing rodent repair deficiency, complementation group 3 (xeroderma pigmentosum group B complementing) | DNA topological change /// transcription-coupled nucleotide-excision repair /// transcription /// regulation of transcription, DNA-dependent /// transcription from RNA polymerase II promoter /// induction of apoptosis /// sensory perception of sound /// DNA repair /// nucleotide-excision repair /// response to DNA damage stimulus /// DNA repair |
| UNG | uracil-DNA glycosylase | carbohydrate metabolism /// DNA repair /// base-excision repair /// response to DNA damage stimulus /// DNA repair |
| ERCC5 | excision repair cross-complementing rodent repair deficiency, complementation group 5 (xeroderma pigmentosum, complementation group G (Cockayne syndrome)) | transcription-coupled nucleotide-excision repair /// nucleotide-excision repair /// sensory perception of sound /// DNA repair /// response to DNA damage stimulus /// nucleotide-excision repair |
| MLH1 | mutL homolog 1, colon cancer, nonpolyposis type 2 (E. coli) | mismatch repair /// cell cycle /// negative regulation of progression through cell cycle /// DNA repair /// mismatch repair /// response to DNA damage stimulus |
| LIG1 | ligase I, DNA, ATP-dependent | DNA replication /// DNA repair /// DNA recombination /// cell cycle /// morphogenesis /// cell division /// DNA repair /// response to DNA damage stimulus /// DNA metabolism |
| NBN | nibrin | DNA damage checkpoint /// cell cycle checkpoint /// double-strand break repair |
| NBN | nibrin | DNA damage checkpoint /// cell cycle checkpoint /// double-strand break repair |

TABLE 3-continued

| Gene Name | Gene Title | Biological Activity |
|---|---|---|
| NBN | nibrin | DNA damage checkpoint /// cell cycle checkpoint /// double-strand break repair |
| MSH6 | mutS homolog 6 (*E. coli*) | mismatch repair /// DNA metabolism /// DNA repair /// mismatch repair /// response to DNA damage stimulus |
| POLD4 | polymerase (DNA-directed), delta 4 | DNA replication /// DNA replication |
| RFC5 | replication factor C (activator 1) 5, 36.5 kDa | DNA replication /// DNA repair /// DNA replication |
| RFC5 | replication factor C (activator 1) 5, 36.5 kDa | DNA replication /// DNA repair /// DNA replication |
| DDB2 /// LHX3 | damage-specific DNA binding protein 2, 48 kDa /// LIM homeobox 3 | nucleotide-excision repair /// regulation of transcription, DNA-dependent /// organ morphogenesis /// DNA repair /// response to DNA damage stimulus /// DNA repair /// transcription /// regulation of transcription |
| POLD1 | polymerase (DNA directed), delta 1, catalytic subunit 125 kDa | DNA replication /// DNA repair /// response to UV /// DNA replication |
| FANCG | Fanconi anemia, complementation group G | cell cycle checkpoint /// DNA repair /// DNA repair /// response to DNA damage stimulus /// regulation of progression through cell cycle |
| POLB | polymerase (DNA directed), beta | DNA-dependent DNA replication /// DNA repair /// DNA replication /// DNA repair /// response to DNA damage stimulus |
| XRCC1 | X-ray repair complementing defective repair in Chinese hamster cells 1 | single strand break repair |
| MPG | N-methylpurine-DNA glycosylase | base-excision repair /// DNA dealkylation /// DNA repair /// base-excision repair /// response to DNA damage stimulus |
| RFC2 | replication factor C (activator 1) 2, 40 kDa | DNA replication |
| ERCC1 | excision repair cross-complementing rodent repair deficiency, complementation group 1 (includes overlapping antisense sequence) | nucleotide-excision repair /// morphogenesis /// nucleotide-excision repair /// DNA repair /// response to DNA damage stimulus |
| TDG | thymine-DNA glycosylase | carbohydrate metabolism /// base-excision repair /// DNA repair /// response to DNA damage stimulus |
| TDG | thymine-DNA glycosylase | carbohydrate metabolism /// base-excision repair /// DNA repair /// response to DNA damage stimulus |
| FANCA | Fanconi anemia, complementation group A /// Fanconi anemia, complementation group A | DNA repair /// protein complex assembly /// DNA repair /// response to DNA damage stimulus |
| RFC4 | replication factor C (activator 1) 4, 37 kDa | DNA replication /// DNA strand elongation /// DNA repair /// phosphoinositide-mediated signaling /// DNA replication |
| RFC3 | replication factor C (activator 1) 3, 38 kDa | DNA replication /// DNA strand elongation |
| RFC3 | replication factor C (activator 1) 3, 38 kDa | DNA replication /// DNA strand elongation |
| APEX2 | APEX nuclease (apurinic/apyrimidinic endonuclease) 2 | DNA repair /// response to DNA damage stimulus |
| RAD1 | RAD1 homolog (*S. pombe*) | DNA repair /// cell cycle checkpoint /// cell cycle checkpoint /// DNA damage checkpoint /// DNA repair /// response to DNA damage stimulus /// meiotic prophase I |
| RAD1 | RAD1 homolog (*S. pombe*) | DNA repair /// cell cycle checkpoint /// cell cycle checkpoint /// DNA damage checkpoint /// DNA repair /// response to DNA damage stimulus /// meiotic prophase I |
| BRCA1 | breast cancer 1, early onset | regulation of transcription from RNA polymerase II promoter /// regulation of transcription from RNA polymerase III promoter /// DNA damage response, signal transduction by p53 class mediator resulting in transcription of p21 class mediator /// cell cycle /// protein ubiquitination /// androgen receptor signaling pathway /// regulation of cell proliferation /// regulation of apoptosis /// positive regulation of DNA repair /// negative regulation of progression through cell cycle /// positive regulation of transcription, DNA-dependent /// negative regulation of centriole replication /// DNA damage response, signal transduction resulting in induction of apoptosis /// DNA repair /// response to DNA damage stimulus /// protein ubiquitination /// DNA repair /// regulation of DNA repair /// apoptosis /// response to DNA damage stimulus |

TABLE 3-continued

| Gene Name | Gene Title | Biological Activity |
|---|---|---|
| EXO1 | exonuclease 1 | DNA repair /// DNA repair /// mismatch repair /// DNA recombination |
| FEN1 | flap structure-specific endonuclease 1 | DNA replication /// double-strand break repair /// UV protection /// phosphoinositide-mediated signaling /// DNA repair /// DNA replication /// DNA repair /// DNA repair |
| FEN1 | flap structure-specific endonuclease 1 | DNA replication /// double-strand break repair /// UV protection /// phosphoinositide-mediated signaling /// DNA repair /// DNA replication /// DNA repair /// DNA repair |
| MLH3 | mutL homolog 3 (*E. coli*) | mismatch repair /// meiotic recombination /// DNA repair /// mismatch repair /// response to DNA damage stimulus /// mismatch repair |
| MGMT | O-6-methylguanine-DNA methyltransferase | DNA ligation /// DNA repair /// response to DNA damage stimulus |
| RAD51 | RAD51 homolog (RecA homolog, *E. coli*) (*S. cerevisiae*) | double-strand break repair via homologous recombination /// DNA unwinding during replication /// DNA repair /// mitotic recombination /// meiosis /// meiotic recombination /// positive regulation of DNA ligation /// protein homooligomerization /// response to DNA damage stimulus /// DNA metabolism /// DNA repair /// response to DNA damage stimulus /// DNA repair /// DNA recombination /// meiotic recombination /// double-strand break repair via homologous recombination /// DNA unwinding during replication |
| RAD51 | RAD51 homolog (RecA homolog, *E. coli*) (*S. cerevisiae*) | double-strand break repair via homologous recombination /// DNA unwinding during replication /// DNA repair /// mitotic recombination /// meiosis /// meiotic recombination /// positive regulation of DNA ligation /// protein homooligomerization /// response to DNA damage stimulus /// DNA metabolism /// DNA repair /// response to DNA damage stimulus /// DNA repair /// DNA recombination /// meiotic recombination /// double-strand break repair via homologous recombination /// DNA unwinding during replication |
| XRCC4 | X-ray repair complementing defective repair in Chinese hamster cells 4 | DNA repair /// double-strand break repair /// DNA recombination /// DNA recombination /// response to DNA damage stimulus |
| XRCC4 | X-ray repair complementing defective repair in Chinese hamster cells 4 | DNA repair /// double-strand break repair /// DNA recombination /// DNA recombination /// response to DNA damage stimulus |
| RECQL | RecQ protein-like (DNA helicase Q1-like) | DNA repair /// DNA metabolism |
| ERCC8 | excision repair cross-complementing rodent repair deficiency, complementation group 8 | DNA repair /// transcription /// regulation of transcription, DNA-dependent /// sensory perception of sound /// transcription-coupled nucleotide-excision repair |
| FANCC | Fanconi anemia, complementation group C | DNA repair /// DNA repair /// protein complex assembly /// response to DNA damage stimulus |
| OGG1 | 8-oxoguanine DNA glycosylase | carbohydrate metabolism /// base-excision repair /// DNA repair /// base-excision repair /// response to DNA damage stimulus /// DNA repair |
| MRE11A | MRE11 meiotic recombination 11 homolog A (*S. cerevisiae*) | regulation of mitotic recombination /// double-strand break repair via nonhomologous end-joining /// telomerase-dependent telomere maintenance /// meiosis /// meiotic recombination /// DNA metabolism /// DNA repair /// double-strand break repair /// response to DNA damage stimulus /// DNA repair /// double-strand break repair /// DNA recombination |
| RAD52 | RAD52 homolog (*S. cerevisiae*) | double-strand break repair /// mitotic recombination /// meiotic recombination /// DNA repair /// DNA recombination /// response to DNA damage stimulus |
| WRN | Werner syndrome | DNA metabolism /// aging |
| XPA | xeroderma pigmentosum, complementation group A | nucleotide-excision repair /// DNA repair /// response to DNA damage stimulus /// DNA repair /// nucleotide-excision repair |
| BLM | Bloom syndrome | DNA replication /// DNA repair /// DNA recombination /// antimicrobial humoral response (sensu Vertebrata) /// DNA metabolism /// DNA replication |

TABLE 3-continued

| Gene Name | Gene Title | Biological Activity |
|---|---|---|
| OGG1 | 8-oxoguanine DNA glycosylase | carbohydrate metabolism /// base-excision repair /// DNA repair /// base-excision repair /// response to DNA damage stimulus /// DNA repair |
| MSH3 | mutS homolog 3 (*E. coli*) | mismatch repair /// DNA metabolism /// DNA repair /// mismatch repair /// response to DNA damage stimulus |
| POLE2 | polymerase (DNA directed), epsilon 2 (p59 subunit) | DNA replication /// DNA repair /// DNA replication |
| RAD51C | RAD51 homolog C (*S. cerevisiae*) | DNA repair /// DNA recombination /// DNA metabolism /// DNA repair /// DNA recombination /// response to DNA damage stimulus |
| LIG4 | ligase IV, DNA, ATP-dependent | single strand break repair /// DNA replication /// DNA recombination /// cell cycle /// cell division /// DNA repair /// response to DNA damage stimulus |
| ERCC6 | excision repair cross-complementing rodent repair deficiency, complementation group 6 | DNA repair /// transcription /// regulation of transcription, DNA-dependent /// transcription from RNA polymerase II promoter /// sensory perception of sound |
| LIG3 | ligase III, DNA, ATP-dependent | DNA replication /// DNA repair /// cell cycle /// meiotic recombination /// spermatogenesis /// cell division /// DNA repair /// DNA recombination /// response to DNA damage stimulus |
| RAD17 | RAD17 homolog (*S. pombe*) | DNA replication /// DNA repair /// cell cycle /// response to DNA damage stimulus |
| XRCC2 | X-ray repair complementing defective repair in Chinese hamster cells 2 | DNA repair /// DNA recombination /// meiosis /// DNA metabolism /// DNA repair /// response to DNA damage stimulus |
| MUTYH | mutY homolog (*E. coli*) | carbohydrate metabolism /// base-excision repair /// mismatch repair /// cell cycle /// negative regulation of progression through cell cycle /// DNA repair /// response to DNA damage stimulus /// DNA repair |
| RFC1 | replication factor C (activator 1) 1, 145 kDa /// replication factor C (activator 1) 1, 145 kDa | DNA-dependent DNA replication /// transcription /// regulation of transcription, DNA-dependent /// telomerase-dependent telomere maintenance /// DNA replication /// DNA repair |
| RFC1 | replication factor C (activator 1) 1, 145 kDa | DNA-dependent DNA replication /// transcription /// regulation of transcription, DNA-dependent /// telomerase-dependent telomere maintenance /// DNA replication /// DNA repair |
| BRCA2 | breast cancer 2, early onset | regulation of progression through cell cycle /// double-strand break repair via homologous recombination /// DNA repair /// establishment and/or maintenance of chromatin architecture /// chromatin remodeling /// regulation of S phase of mitotic cell cycle /// mitotic checkpoint /// regulation of transcription /// response to DNA damage stimulus |
| RAD50 | RAD50 homolog (*S. cerevisiae*) | regulation of mitotic recombination /// double-strand break repair /// telomerase-dependent telomere maintenance /// cell cycle /// meiosis /// meiotic recombination /// chromosome organization and biogenesis /// telomere maintenance /// DNA repair /// response to DNA damage stimulus /// DNA repair /// DNA recombination |
| DDB1 | damage-specific DNA binding protein 1, 127 kDa | nucleotide-excision repair /// ubiquitin cycle /// DNA repair /// response to DNA damage stimulus /// DNA repair |
| XRCC5 | X-ray repair complementing defective repair in Chinese hamster cells 5 (double-strand-break rejoining; Ku autoantigen, 80 kDa) | double-strand break repair via nonhomologous end-joining /// DNA recombination /// DNA repair /// DNA recombination /// response to DNA damage stimulus /// double-strand break repair |
| XRCC5 | X-ray repair complementing defective repair in Chinese hamster cells 5 (double-strand-break rejoining; Ku autoantigen, 80 kDa) | double-strand break repair via nonhomologous end-joining /// DNA recombination /// DNA repair /// DNA recombination /// response to DNA damage stimulus /// double-strand break repair |
| PARP1 | poly (ADP-ribose) polymerase family, member 1 | DNA repair /// transcription from RNA polymerase II promoter /// protein amino acid ADP-ribosylation /// DNA metabolism /// DNA repair /// protein amino acid ADP-ribosylation /// response to DNA damage stimulus |
| POLE3 | polymerase (DNA directed), epsilon 3 (p17 subunit) | DNA replication |
| RFC1 | replication factor C (activator 1) 1, 145 kDa | DNA-dependent DNA replication /// transcription /// regulation of transcription, DNA-dependent /// telomerase-dependent telomere maintenance /// DNA replication /// DNA repair |
| RAD50 | RAD50 homolog (*S. cerevisiae*) | regulation of mitotic recombination /// double-strand break repair /// telomerase-dependent telomere maintenance /// cell cycle /// meiosis /// meiotic recombination /// chromosome organization |

TABLE 3-continued

| Gene Name | Gene Title | Biological Activity |
|---|---|---|
| | | and biogenesis /// telomere maintenance /// DNA repair /// response to DNA damage stimulus /// DNA repair /// DNA recombination |
| XPC | xeroderma pigmentosum, complementation group C | nucleotide-excision repair /// DNA repair /// nucleotide-excision repair /// response to DNA damage stimulus /// DNA repair |
| MSH2 | mutS homolog 2, colon cancer, nonpolyposis type 1 (*E. coli*) | mismatch repair /// postreplication repair /// cell cycle /// negative regulation of progression through cell cycle /// DNA metabolism /// DNA repair /// mismatch repair /// response to DNA damage stimulus /// DNA repair |
| RPA3 | replication protein A3, 14 kDa | DNA replication /// DNA repair /// DNA replication |
| MBD4 | methyl-CpG binding domain protein 4 | base-excision repair /// DNA repair /// response to DNA damage stimulus /// DNA repair |
| MBD4 | methyl-CpG binding domain protein 4 | base-excision repair /// DNA repair /// response to DNA damage stimulus /// DNA repair |
| NTHL1 | nth endonuclease III-like 1 (*E. coli*) | carbohydrate metabolism /// base-excision repair /// nucleotide-excision repair, DNA incision, 5'-to lesion /// DNA repair /// response to DNA damage stimulus |
| PMS2 /// PMS2CL | PMS2 postmeiotic segregation increased 2 (*S. cerevisiae*) /// PMS2-C terminal-like | mismatch repair /// cell cycle /// negative regulation of progression through cell cycle /// DNA repair /// mismatch repair /// response to DNA damage stimulus /// mismatch repair |
| RAD51C | RAD51 homolog C (*S. cerevisiae*) | DNA repair /// DNA recombination /// DNA metabolism /// DNA repair /// DNA recombination /// response to DNA damage stimulus |
| UNG2 | uracil-DNA glycosylase 2 | regulation of progression through cell cycle /// carbohydrate metabolism /// base-excision repair /// DNA repair /// response to DNA damage stimulus |
| APEX1 | APEX nuclease (multifunctional DNA repair enzyme) 1 | base-excision repair /// transcription from RNA polymerase II promoter /// regulation of DNA binding /// DNA repair /// response to DNA damage stimulus |
| ERCC4 | excision repair cross-complementing rodent repair deficiency, complementation group 4 | nucleotide-excision repair /// nucleotide-excision repair /// DNA metabolism /// DNA repair /// response to DNA damage stimulus |
| RAD1 | RAD1 homolog (*S. pombe*) | DNA repair /// cell cycle checkpoint /// cell cycle checkpoint /// DNA damage checkpoint /// DNA repair /// response to DNA damage stimulus /// meiotic prophase I |
| RECQL5 | RecQ protein-like 5 | DNA repair /// DNA metabolism /// DNA metabolism |
| MSH5 | mutS homolog 5 (*E. coli*) | DNA metabolism /// mismatch repair /// mismatch repair /// meiosis /// meiotic recombination /// meiotic prophase II /// meiosis |
| RECQL | RecQ protein-like (DNA helicase Q1-like) | DNA repair /// DNA metabolism |
| RAD52 | RAD52 homolog (*S. cerevisiae*) | double-strand break repair /// mitotic recombination /// meiotic recombination /// DNA repair /// DNA recombination /// response to DNA damage stimulus |
| XRCC4 | X-ray repair complementing defective repair in Chinese hamster cells 4 | DNA repair /// double-strand break repair /// DNA recombination /// DNA recombination /// response to DNA damage stimulus |
| XRCC4 | X-ray repair complementing defective repair in Chinese hamster cells 4 | DNA repair /// double-strand break repair /// DNA recombination /// DNA recombination /// response to DNA damage stimulus |
| RAD17 | RAD17 homolog (*S. pombe*) | DNA replication /// DNA repair /// cell cycle /// response to DNA damage stimulus |
| MSH3 | mutS homolog 3 (*E. coli*) | mismatch repair /// DNA metabolism /// DNA repair /// mismatch repair /// response to DNA damage stimulus |
| MRE11A | MRE11 meiotic recombination 11 homolog A (*S. cerevisiae*) | regulation of mitotic recombination /// double-strand break repair via nonhomologous end-joining /// telomerase-dependent telomere maintenance /// meiosis /// meiotic recombination /// DNA metabolism /// DNA repair /// double-strand break repair /// response to DNA damage stimulus /// DNA repair /// double-strand break repair /// DNA recombination |
| MSH6 | mutS homolog 6 (*E. coli*) | mismatch repair /// DNA metabolism /// DNA repair /// mismatch repair /// response to DNA damage stimulus |
| MSH6 | mutS homolog 6 (*E. coli*) | mismatch repair /// DNA metabolism /// DNA repair /// mismatch repair /// response to DNA damage stimulus |
| RECQL5 | RecQ protein-like 5 | DNA repair /// DNA metabolism /// DNA metabolism |
| BRCA1 | breast cancer 1, early onset | regulation of transcription from RNA polymerase II promoter /// regulation of transcription from RNA |

TABLE 3-continued

| Gene Name | Gene Title | Biological Activity |
| --- | --- | --- |
| | | polymerase III promoter /// DNA damage response, signal transduction by p53 class mediator resulting in transcription of p21 class mediator /// cell cycle /// protein ubiquitination /// androgen receptor signaling pathway /// regulation of cell proliferation /// regulation of apoptosis /// positive regulation of DNA repair /// negative regulation of progression through cell cycle /// positive regulation of transcription, DNA-dependent /// negative regulation of centriole replication /// DNA damage response, signal transduction resulting in induction of apoptosis /// DNA repair /// response to DNA damage stimulus /// protein ubiquitination /// DNA repair /// regulation of DNA repair /// apoptosis /// response to DNA damage stimulus |
| RAD52 | RAD52 homolog (*S. cerevisiae*) | double-strand break repair /// mitotic recombination /// meiotic recombination /// DNA repair /// DNA recombination /// response to DNA damage stimulus |
| POLD3 | polymerase (DNA-directed), delta 3, accessory subunit | DNA synthesis during DNA repair /// mismatch repair /// DNA replication |
| MSH5 | mutS homolog 5 (*E. coli*) | DNA metabolism /// mismatch repair /// mismatch repair /// meiosis /// meiotic recombination /// meiotic prophase II /// meiosis |
| ERCC2 | excision repair cross-complementing rodent repair deficiency, complementation group 2 (xeroderma pigmentosum D) | transcription-coupled nucleotide-excision repair /// transcription /// regulation of transcription, DNA-dependent /// transcription from RNA polymerase II promoter /// induction of apoptosis /// sensory perception of sound /// nucleobase, nucleoside, nucleotide and nucleic acid metabolism /// nucleotide-excision repair |
| RECQL4 | RecQ protein-like 4 | DNA repair /// development /// DNA metabolism |
| PMS1 | PMS1 postmeiotic segregation increased 1 (*S. cerevisiae*) | mismatch repair /// regulation of transcription, DNA-dependent /// cell cycle /// negative regulation of progression through cell cycle /// mismatch repair /// DNA repair /// response to DNA damage stimulus |
| ZFP276 | zinc finger protein 276 homolog (mouse) | transcription /// regulation of transcription, DNA-dependent |
| MBD4 | methyl-CpG binding domain protein 4 | base-excision repair /// DNA repair /// response to DNA damage stimulus /// DNA repair |
| MBD4 | methyl-CpG binding domain protein 4 | base-excision repair /// DNA repair /// response to DNA damage stimulus /// DNA repair |
| MLH3 | mutL homolog 3 (*E. coli*) | mismatch repair /// meiotic recombination /// DNA repair /// mismatch repair /// response to DNA damage stimulus /// mismatch repair |
| FANCA | Fanconi anemia, complementation group A | DNA repair /// protein complex assembly /// DNA repair /// response to DNA damage stimulus |
| POLE | polymerase (DNA directed), epsilon | DNA replication /// DNA repair /// DNA replication /// response to DNA damage stimulus |
| XRCC3 | X-ray repair complementing defective repair in Chinese hamster cells 3 | DNA repair /// DNA recombination /// DNA metabolism /// DNA repair /// DNA recombination /// response to DNA damage stimulus /// response to DNA damage stimulus |
| MLH3 | mutL homolog 3 (*E. coli*) | mismatch repair /// meiotic recombination /// DNA repair /// mismatch repair /// response to DNA damage stimulus /// mismatch repair |
| NBN | nibrin | DNA damage checkpoint /// cell cycle checkpoint /// double-strand break repair |
| SMUG1 | single-strand selective monofunctional uracil DNA glycosylase | carbohydrate metabolism /// DNA repair /// response to DNA damage stimulus |
| FANCF | Fanconi anemia, complementation group F | DNA repair /// response to DNA damage stimulus |
| NEIL1 | nei endonuclease VIII-like 1 (*E. coli*) | carbohydrate metabolism /// DNA repair /// response to DNA damage stimulus |
| FANCE | Fanconi anemia, complementation group E | DNA repair /// response to DNA damage stimulus |
| MSH5 | mutS homolog 5 (*E. coli*) | DNA metabolism /// mismatch repair /// mismatch repair /// meiosis /// meiotic recombination /// meiotic prophase II /// meiosis |
| RECQL5 | RecQ protein-like 5 | DNA repair /// DNA metabolism /// DNA metabolism |

For still another example, some cell free DNAs/mRNAs are fragments of or those encoding a full length or a fragment of a gene not associated with a disease (e.g., housekeeping genes), including, but not limited to, those related to transcription factors (e.g., ATF1, ATF2, ATF4, ATF6, ATF7, ATFIP, BTF3, E2F4, ERH, HMGB1, ILF2, IER2, JUND, TCEB2, etc.), repressors (e.g., PUF60), RNA splicing (e.g., BAT1, HNRPD, HNRPK, PABPN1, SRSF3, etc.), translation factors (EIF1, EIF1AD, EIF1B, EIF2A, EIF2AK1, EIF2AK3, EIF2AK4, EIF2B2, EIF2B3, EIF2B4, EIF2S2, EIF3A, etc.), tRNA synthetases (e.g., AARS, CARS, DARS, FARS, GARS, HARS, TARS, KARS, MARS, etc.), RNA binding protein (e.g., ELAVL1, etc.), ribosomal proteins (e.g., RPL5, RPL8, RPL9, RPL10, RPL11, RPL14, RPL25, etc.), mitochondrial ribosomal proteins (e.g., MRPL9, MRPL1, MRPL10, MRPL11, MRPL12, MRPL13, MRPL14, etc.), RNA polymerase (e.g., POLR1C, POLR1D, POLR1E, POLR2A, POLR2B, POLR2C, POLR2D, POLR3C, etc.), protein processing (e.g., PPID, PPI3, PPIF, CANX, CAPN1, NACA, PFDN2, SNX2, SS41, SUMO1, etc.), heat shock proteins (e.g., HSPA4, HSPA5, HSBP1, etc.), histone (e.g., HIST1HSBC, H1FX, etc.), cell cycle (e.g., ARHGAP35, RAB 10, RAB 11A, CCNY, CCNL, PPP1CA, RAD1, RAD17, etc.), carbohydrate metabolism (e.g., ALDOA, GSK3A, PGK1, PGAM5, etc.), lipid metabolism (e.g., HADHA), citric acid cycle (e.g., SDHA, SDHB, etc.), amino acid metabolism (e.g., COMT, etc.), NADH dehydrogenase (e.g., NDUFA2, etc.), cytochrome c oxidase (e.g., COX5B, COX8, COX11, etc.), ATPase (e.g. ATP2C1, ATP5F1, etc.), lysosome (e.g., CTSD, CSTB, LAMP1, etc.), proteasome (e.g., PSMA1, UBA1, etc.), cytoskeletal proteins (e.g., ANXA6, ARPC2, etc.), and organelle synthesis (e.g., BLOC1S1, AP2A1, etc.).

In still another example, some cell free DNAs/mRNAs are fragments of or those encoding a full length or a fragment of a neoepitope specific to the tumor. With respect to neoepitope, it should be appreciated that neoepitopes can be characterized as random mutations in tumor cells that create unique and tumor specific antigens. Therefore, high-throughput genome sequencing should allow for rapid and specific identification of patient specific neoepitopes where the analysis also considers matched normal tissue of the same patient. In some embodiments, neoepitopes may be identified from a patient tumor in a first step by whole genome analysis of a tumor biopsy (or lymph biopsy or biopsy of a metastatic site) and matched normal tissue (i.e., non-diseased tissue from the same patient) via synchronous comparison of the so obtained omics information. While not limiting to the inventive subject matter, it is typically preferred that the data are patient matched tumor data (e.g., tumor versus same patient normal), and that the data format is in SAM, BAM, GAR, or VCF format. However, non-matched or matched versus other reference (e.g., prior same patient normal or prior same patient tumor, or homo statisticus) are also deemed suitable for use herein. Therefore, the omics data may be 'fresh' omics data or omics data that were obtained from a prior procedure (or even different patient). However, and especially where genomics ctDNA is analyzed, the neoepitope-coding sequence need not necessarily be expressed.

In particularly preferred aspects, the nucleic acid encoding a neoepitope may encode a neoepitope that is also a suitable target for immune therapy. Therefore, neoepitopes can then be further filtered for a match to the patient's HLA type to thereby increase likelihood of antigen presentation of the neoepitope. Most preferably, and as further discussed below, such matching can be done in silico. Most typically, the patient-specific epitopes are unique to the patient, but may also in at least some cases include tumor type-specific neoepitopes (e.g., Her-2, PSA, brachyury) or cancer-associated neoepitopes (e.g., CEA, MUC-1, CYPB1).

It is contemplated that cell free DNA/mRNA may present in modified forms or different isoforms. For example, the cell free DNA may be present in methylated or hydroxyl methylated, and the methylation level of some genes (e.g., GSTP1, p16, APC, etc.) may be a hallmark of specific types of cancer (e.g., colorectal cancer, etc.). The cell free mRNA may be present in a plurality of isoforms (e.g., splicing variants, etc.) that may be associated with different cell types and/or location. Preferably, different isoforms of mRNA may be a hallmark of specific tissues (e.g., brain, intestine, adipose tissue, muscle, etc.), or may be a hallmark of cancer (e.g., different isoform is present in the cancer cell compared to corresponding normal cell, or the ratio of different isoforms is different in the cancer cell compared to corresponding normal cell, etc.). For example, mRNA encoding HMGB1 are present in 18 different alternative splicing variants and 2 unspliced forms. Those isoforms are expected to express in different tissues/locations of the patient's body (e.g., isoform A is specific to prostate, isoform B is specific to brain, isoform C is specific to spleen, etc.). Thus, in these embodiments, identifying the isoforms of cell free mRNA in the patient's bodily fluid can provide information on the origin (e.g., cell type, tissue type, etc.) of the cell free mRNA.

The inventors contemplate that the quantities and/or isoforms (or subtypes) or regulatory noncoding RNA (e.g., microRNA, small interfering RNA, long non-coding RNA (lncRNA)) can vary and fluctuate by presence of a tumor or immune response against the tumor. Without wishing to be bound by any specific theory, varied expression of regulatory noncoding RNA in a cancer patient's bodily fluid may due to genetic modification of the cancer cell (e.g., deletion, translocation of parts of a chromosome, etc.), and/or inflammations at the cancer tissue by immune system (e.g., regulation of miR-29 family by activation of interferon signaling and/or virus infection, etc.). Thus, in some embodiments, the cell free RNA can be a regulatory noncoding RNA that modulates expression (e.g., downregulates, silences, etc.) of mRNA encoding a cancer-related protein or an inflammation-related protein (e.g., HMGB1, HMGB2, HMGB3, MUC1, VWF, MMP, CRP, PBEF1, TNF-α, TGF-β, PDGFA, IL-1, IL-2, IL-3, IL-4, IL-5, IL-6, IL-7, IL-8, IL-9, IL-10, IL-12, IL-13, IL-15, IL-17, Eotaxin, FGF, G-CSF, GM-CSF, IFN-γ, IP-10, MCP-1, PDGF, hTERT, etc.).

It is also contemplated that some cell free regulatory noncoding RNA may be present in a plurality of isoforms or members (e.g., members of miR-29 family, etc.) that may be associated with different cell types and/or location. Preferably, different isoforms or members of regulatory noncoding RNA may be a hallmark of specific tissues (e.g., brain, intestine, adipose tissue, muscle, etc.), or may be a hallmark of cancer (e.g., different isoform is present in the cancer cell compared to corresponding normal cell, or the ratio of different isoforms is different in the cancer cell compared to corresponding normal cell, etc.). For example, higher expression level of miR-155 in the bodily fluid can be associated with the presence of breast tumor, and the reduced expression level of miR-155 can be associated with reduced size of breast tumor. Thus, in these embodiments, identifying the isoforms of cell free regulatory noncoding RNA in the patient's bodily fluid can provide information on the origin (e.g., cell type, tissue type, etc.) of the cell free regulatory noncoding RNA.

Isolation and Amplification of Cell Free DNA/RNA

Any suitable methods to isolate and amplify cell free DNA/RNA are contemplated. Most typically, cell free DNA/RNA is isolated from a bodily fluid (e.g., whole blood) that is processed under a suitable conditions, including a condition that stabilizes cell free RNA. Preferably, both cell free DNA and RNA are isolated simultaneously from the same badge of the patient's bodily fluid. Yet, it is also contemplated that the bodily fluid sample can be divided into two or more smaller samples from which DNA or RNA can be isolated separately. Once separated from the non-nucleic acid components, cell free RNA are then quantified, preferably using real time, quantitative PCR or real time, quantitative RT-PCR.

The bodily fluid of the patient can be obtained at any desired time point(s) depending on the purpose of the omics analysis. For example, the bodily fluid of the patient can be obtained before and/or after the patient is confirmed to have a tumor and/or periodically thereafter (e.g., every week, every month, etc.) in order to associate the cell free DNA/RNA data with the prognosis of the cancer. In some embodiments, the bodily fluid of the patient can be obtained from a patient before and after the cancer treatment (e.g., chemotherapy, radiotherapy, drug treatment, cancer immunotherapy, etc.). While it may vary depending on the type of treatments and/or the type of cancer, the bodily fluid of the patient can be obtained at least 24 hours, at least 3 days, at least 7 days after the cancer treatment. For more accurate comparison, the bodily fluid from the patient before the cancer treatment can be obtained less than 1 hour, less than 6 hours before, less than 24 hours before, less than a week before the beginning of the cancer treatment. In addition, a plurality of samples of the bodily fluid of the patient can be obtained during a period before and/or after the cancer treatment (e.g., once a day after 24 hours for 7 days, etc.).

Additionally or alternatively, the bodily fluid of a healthy individual can be obtained to compare the sequence/modification of cell free DNA, and/or quantity/subtype expression of cell free RNA. As used herein, a healthy individual refers an individual without a tumor. Preferably, the healthy individual can be chosen among group of people shares characteristics with the patient (e.g., age, gender, ethnicity, diet, living environment, family history, etc.).

Any suitable methods for isolating cell free DNA/RNA are contemplated. For example, in one exemplary method of DNA isolation, specimens were accepted as 10 ml of whole blood drawn into a test tube. Cell free DNA can be isolated from other from mono-nucleosomal and di-nucleosomal complexes using magnetic beads that can separate out cell free DNA at a size between 100-300 bps. For another example, in one exemplary method of RNA isolation, specimens were accepted as 10 ml of whole blood drawn into cell-free RNA BCT® tubes or cell-free DNA BCT® tubes containing RNA stabilizers, respectively. Advantageously, cell free RNA is stable in whole blood in the cell-free RNA BCT tubes for seven days while cell free RNA is stable in whole blood in the cell-free DNA BCT Tubes for fourteen days, allowing time for shipping of patient samples from world-wide locations without the degradation of cell free RNA. Moreover, it is generally preferred that the cell free RNA is isolated using RNA stabilization agents that will not or substantially not (e.g., equal or less than 1%, or equal or less than 0.1%, or equal or less than 0.01%, or equal or less than 0.001%) lyse blood cells. Viewed from a different perspective, the RNA stabilization reagents will not lead to a substantial increase (e.g., increase in total RNA no more than 10%, or no more than 5%, or no more than 2%, or no more than 1%) in RNA quantities in serum or plasma after the reagents are combined with blood. Likewise, these reagents will also preserve physical integrity of the cells in the blood to reduce or even eliminate release of cellular RNA found in blood cell. Such preservation may be in form of collected blood that may or may not have been separated. In less preferred aspects, contemplated reagents will stabilize cell free RNA in a collected tissue other than blood for at 2 days, more preferably at least 5 days, and most preferably at least 7 days. Of course, it should be recognized that numerous other collection modalities are also deemed appropriate, and that the cell free RNA can be at least partially purified or adsorbed to a solid phase to so increase stability prior to further processing.

As will be readily appreciated, fractionation of plasma and extraction of cell free DNA/RNA can be done in numerous manners. In one exemplary preferred aspect, whole blood in 10 mL tubes is centrifuged to fractionate plasma at 1600 rcf for 20 minutes. The so obtained plasma is then separated and centrifuged at 16,000 rcf for 10 minutes to remove cell debris. Of course, various alternative centrifugal protocols are also deemed suitable so long as the centrifugation will not lead to substantial cell lysis (e.g., lysis of no more than 1%, or no more than 0.1%, or no more than 0.01%, or no more than 0.001% of all cells). Cell free RNA is extracted from 2 mL of plasma using Qiagen reagents. The extraction protocol was designed to remove potential contaminating blood cells, other impurities, and maintain stability of the nucleic acids during the extraction. All nucleic acids were kept in bar-coded matrix storage tubes, with DNA stored at −4° C. and RNA stored at −80° C. or reverse-transcribed to cDNA that is then stored at −4° C. Notably, so isolated cell free RNA can be frozen prior to further processing.

Omics Data Processing

Once cell free DNA/RNA is isolated, various types of omics data can be obtained using any suitable methods. DNA sequence data will not only include the presence or absence of a gene that is associated with cancer or inflammation, but also take into account mutation data where the gene is mutated, the copy number (e.g., to identify duplication, loss of allele or heterozygosity), and epigenetic status (e.g., methylation, histone phosphorylation, nucleosome positioning, etc.). With respect to RNA sequence data it should be noted that contemplated RNA sequence data include mRNA sequence data, splice variant data, polyadenylation information, etc. Moreover, it is generally preferred that the RNA sequence data also include a metric for the transcription strength (e.g., number of transcripts of a damage repair gene per million total transcripts, number of transcripts of a damage repair gene per total number of transcripts for all damage repair genes, number of transcripts of a damage repair gene per number of transcripts for actin or other household gene RNA, etc.), and for the transcript stability (e.g., a length of poly A tail, etc.).

With respect to the transcription strength (expression level), transcription strength of the cell free RNA can be examined by quantifying the cell free RNA. Quantification of cell free RNA can be performed in numerous manners, however, expression of analytes is preferably measured by quantitative real-time RT-PCR of cell free RNA using primers specific for each gene. For example, amplification can be performed using an assay in a 10 μL reaction mix containing 2 μL cell free RNA, primers, and probe. mRNA of α-actin can be used as an internal control for the input level of cell free RNA. A standard curve of samples with known concentrations of each analyte was included in each PCR plate as well as positive and negative controls for each gene. Test samples were identified by scanning the 2D barcode on the matrix tubes containing the nucleic acids. Delta Ct (dCT) was calculated from the Ct value derived from quantitative PCR (qPCR) amplification for each analyte subtracted by the Ct value of actin for each individual patient's blood sample. Relative expression of patient specimens is calculated using a standard curve of delta Cts of serial dilutions of Universal Human Reference RNA set at a gene expression value of 10 (when the delta CTs were plotted against the log concentration of each analyte).

Alternatively, where discovery or scanning for new mutations or changes in expression of a particular gene is desired, real time quantitative PCR may be replaced by RNAseq to so cover at least part of a patient transcriptome. Moreover, it should be appreciated that analysis can be performed static or over a time course with repeated sampling to obtain a dynamic picture without the need for biopsy of the tumor or a metastasis.

Thus, omics data of cell free DNA/RNA preferably comprise a genomic data set that includes genomic sequence information. Most typically, the genomic sequence information comprises DNA sequence information of cell free DNA of the patient and optionally cell free DNA of a healthy individual. The sequence data sets may include unprocessed or processed data sets, and exemplary data sets include those having BAM format, SAM format, FASTQ format, or FASTA format. However, it is especially preferred that the data sets are provided in BAM format or as BAMBAM diff objects (see e.g., US2012/0059670A1 and US2012/0066001A1). Moreover, it should be noted that the data sets are reflective of the cell free DNA/RNA of the patient and of the healthy individual to so obtain patient and tumor specific information. Thus, genetic germ line alterations not giving rise to the diseased cells (e.g., silent mutation, SNP, etc.) can be excluded. Further, so obtained omics information can then be processed using pathway analysis (especially using PARADIGM) to identify any impact of any mutations on DNA repair pathways.

Likewise, computational analysis of the sequence data may be performed in numerous manners. In most preferred methods, however, analysis is performed in silico by location-guided synchronous alignment of cell free DNA/RNA of the patient and a healthy individual as, for example, disclosed in US 2012/0059670A1 and US 2012/0066001A1 using BAM files and BAM servers. Such analysis advantageously reduces false positive data and significantly reduces demands on memory and computational resources.

With respect to the analysis of cell free DNA/RNA of the patient and a healthy individual, numerous manners are deemed suitable for use herein so long as such methods will be able to generate a differential sequence object. However, it is especially preferred that the differential sequence object is generated by incremental synchronous alignment of BAM files representing genomic sequence information of the cell free DNA/RNA of the patient and a healthy individual. For example, particularly preferred methods include BAM-BAM-based methods as described in US 2012/0059670 and US 2012/0066001.

One should appreciate the computing devices comprise a processor configured to execute software instructions stored on a tangible, non-transitory computer readable storage medium (for example, hard drive, solid state drive, RAM, flash, ROM, memory card, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

BamBam is a tool that simultaneously analyzes each genomic position from a patient's tumor and germline genomes using the aligned short-read data contained in SAM/BAM-formatted files (SAMtools library; Li H, Handsaker B, Wysoker A, Fennell T, Ruan J, Homer N, Marth G, Abecasis G, Durbin R; 1000 Genome Project Data Processing Subgroup. The Sequence Alignment/Map format and SAMtools. Bioinformatics. 2009 Aug. 15; 25 (16):2078-9. Epub 2009 Jun. 8). BamBam interfaces with the SAMtools library to simultaneously analyze a patient's tumor and germline genomes using short-read alignments from SAM/BAM-formatted files. In the present disclosure the BamBam tool can be a sequence analysis engine that is used to compare sequences, the sequences comprising strings of information. In one embodiment, the strings of information comprise biological information, for example, a polynucleotide sequence or a polypeptide sequence. In another embodiment, the biological information can comprise expression data, for example relative concentration levels of mRNA transcripts or rRNA or tRNA or peptide or polypeptide or protein. In another embodiment, the biological information can be relative amounts of protein modification, such as for example, but not limited to, phosphorylation, sulphation, actylation, methylation, glycosilation, sialation, modification with glycosylphosphatidylinositol, or modification with proteoglycan.

This method of processing enables BamBam to efficiently calculate overall copy number and infer regions of structural variation (for example, chromosomal translocations) in both tumor and germline genomes; to efficiently calculate overall and allele-specific copy number; infer regions exhibiting loss of heterozygosity (LOH); and discover both somatic and germline sequence variants (for example, point mutations) and structural rearrangements (for example, chromosomal fusions. Furthermore, by comparing the two genome sequences at the same time, BamBam can also immediately distinguish somatic from germline sequence variants, calculate allele-specific copy number alterations in the tumor genome, and phase germline haplotypes across chromosomal regions where the allelic proportion has shifted in the tumor genome. By bringing together all of these analyses into a single tool, researchers can use BamBam to discover many types of genomic alterations that occurred within a patient's tumor genome, often to specific gene alleles, that help to identify potential drivers of tumorigenesis.

To determine if a variant discovered is somatic (that is, a variant sequence found only in the tumor) or a germline (that is, a variant sequence that is inherited or heritable) variant requires that we compare the tumor and matched normal genomes in some way. This can be done sequentially, by summarizing data at every genomic position for both tumor and germline and then combining the results for analysis. Unfortunately, because whole-genome BAM files are hundreds of gigabytes in their compressed form (1-2 terabytes uncompressed), the intermediate results that would need to be stored for later analysis will be extremely large and slow to merge and analyze.

To avoid this issue, BamBam reads from two files at the same time, constantly keeping each BAM file in synchrony with the other and piling up the genomic reads that overlap every common genomic location between the two files. For each pair of pileups, BamBam runs a series of analyses listed above before discarding the pileups and moving to the next common genomic location. By processing these massive BAM files with this method, the computer's RAM usage is minimal and processing speed is limited primarily by the speed that the filesystem can read the two files. This enables BamBam to process massive amounts of data quickly, while being flexible enough to run on a single computer or across a computer cluster. Another important benefit to processing these files with BamBam is that its output is fairly minimal, consisting only of the important differences found in each file. This produces what is essentially a whole-genome diff between the patient's tumor and germline genomes, requiring much less disk storage than it would take if all genome information was stored for each file separately.

BamBam is a computationally efficient method for surveying large sequencing datasets to produce a set of high-quality genomic events that occur within each tumor relative to its germline. These results provide a glimpse into the chromosomal dynamics of tumors, improving our understanding of tumors' final states and the events that led to them. An exemplary scheme of BamBam Data Flow is shown at FIG. 1 of US 2012/0059670.

One particular exemplary embodiment of the invention is creation and use of a differential genetic sequence object. As used herein, the object represents a digital object instantiated from the BamBam techniques and reflects a difference between a reference sequence (for example, a first sequence) and an analysis sequence (for example, a second sequence). The object may be considered a choke point on many different markets. One might consider the following factors related to use and management of such objects from a market perspective:
   a. An object can be dynamic and change with respect to a vector of parameters (for example, time, geographic region, genetic tree, species, etc.)
   b. Objects can be considered to have a "distance" relative to each other objects or reference sequences. The distance can be measured according to dimensions of relevance. For example, the distance can be a deviation from a hypothetical normal or a drift with respect to time.
   c. Objects can be indicative of risk: risk of developing disease, susceptibility to exposure, risk to work at a location, etc.
   d. Objects can be managed for presentation to stakeholders: health care providers, insurers, patients, etc.
   e. Can be presented as a graphical object
   f. Can be presented in a statistical format: single person, a population, a canonical human, etc.

A reference sequence can be generated from the objects to form a normalized sequence. The normalized sequence can be built based on consensus derived from measured objects.

Objects are representative of large sub-genomic or genomic information rather than single-gene alignments and are annotated/contain meta data readable by standard software.

Objects can have internal patterns or structures which can be detected: a set of mutations in one spot might correlate to a second set of mutations in another spot which correlates to a condition; constellation of difference patterns could be a hot spot; use multi-variate analysis or other AI techniques to identify correlations; detect significance of a hot spot (for example, presence, absence, etc.)

Objects related to a single person could be used as a security key

Updating a differential sequence object: Update includes creating, modifying, changing, deleting, etc.; Can be based on a template; Can be a de novo object; Can be an existing object.

Omics Data Analysis: Calculation of a Score

For calculation of a score, it should be appreciated that all data from ct/cf nucleic acids are deemed suitable for use herein and may therefore be specific to a particular tumor and/or patient and/or specific to a cancer. Furthermore, such data may be further normalized or otherwise preprocessed to adjust for age, treatment, gender, stage of disease, etc.

For example, in one aspect of the inventive subject matter the inventors contemplate that a library or reference base for all cancer-related genes, inflammation-related genes, DNA repair-related genes, and/or other non-disease related housekeeping genes can be created using one or more omics data for each of those genes, and such library is particularly useful where the omics data are associated with one or more health parameter. Viewed from a different perspective, while traditional methods of determining cancer prognosis or predicting treatment outcome have been based on a few number of genes, such library can provide a tool to generate a large cross-sectional database for all cancer-related gene activity, inflammation-related gene activity, DNA repair gene activity and housekeeping gene activity (as a control). The large cross-sectional database can be a basis for generating a cancer matrix, based on which a prognosis of a cancer, a health status of the patient, a likelihood of outcome of treatment, an effectiveness of the treatment can be more reliably calculated.

Of course, it should be appreciated that analyses presented herein may be performed over specific and diverse populations to so obtain reference values for the specific populations, such as across various health associated states (e.g., healthy, diagnosed with a specific disease and/or disease state, which may or may not be inherited, or which may or may not be associated with impaired DNA repair, inflammation-related autoimmunity, etc.), a specific age or age bracket, a specific ethnic group that may or may not be associated with frequent occurrence of specific type of cancer. Of course, populations may also be enlisted from databases with known omics information, and especially publically available omics information from cancer patients (e.g., TCGA, COSMIC, etc.) and proprietary databases from a large variety of individuals that may be healthy or diagnosed with a disease. Likewise, it should be appreciated that the population records may also be indexed over time for the same individual or group of individuals, which advantageously allows detection of shifts or changes in the genes and pathways associated with different types of cancers.

In further particularly preferred aspects, it is contemplated that a cancer score can be established for one or more cancer-related genes, inflammation-related genes, a DNA-repair gene, a neoepitope, and a gene not associated with a disease and that the score may be reflective of or even prognostic for various types of cancer that are at least in part due to mutations in cancer-related genes and/or pathways. For example, especially suitable cancer scores may involve scores for one or more genes associated with one or more types of cancer (e.g., BRCA1, BRCA2, P53, etc.) relative to another gene that may or may not be associated with one type of cancer (e.g., housekeeping genes, etc.). In another example, contemplated cancer scores may involve scores for one or more genes associated with one or more types of one or more types of cancer (e.g., BRCA1, BRCA2, P53, etc.)

relative to an overall mutation rate (e.g., mutation rate of the genes not associated with a disease, etc.) to so better identify cancer relevant mutations over 'background' mutations.

Additionally, the omics data may be used to generate a general error status for an individual (or tumor within an individual), or to associate the number and/or type of alterations in cancer-related genes, inflammation-related genes, or a DNA-repair gene to identify a 'tipping point' for one or more gene mutations after which a general mutation rate skyrockets. For example, where a rate or number of mutations in ERCC1 and other DNA repair genes could have only minor systemic consequence, addition of further mutations to TP53 may result in a catastrophic increase in mutation rates. Thus, and viewed from a different perspective, mutations in the genes associated with DNA may be used to estimate the risk of occurrence for a DNA damage-based disease, and especially cancer and age-related diseases. In still further contemplated uses, so obtained omics information may be analyzed in one or more pathway analysis algorithms (e.g., PARADIGM) to so identify affected pathways and to so possibly adjust treatment where treatment employs DNA damaging agents. Pathway analysis algorithms may also be used to in silico modulate expression of one or more DNA repair genes, which may results in desirable or even unexpected in silico treatment outcomes, which may be translated into the clinic.

With respect to calculation, the inventors contemplate that the cancer score is typically a compound score reflecting status of a plurality of genes. For example, the cancer score can be calculated by counting any mutations (e.g., deletion, missense, nonsense, etc.) of any cancer-related genes, inflammation-related genes, and DNA-repair genes with one or more mutations as having a positive value, counting any changes in methylation or other modifications in DNA of counting any cancer-related genes, DNA-repair genes, counting any upregulation or downregulation in expression levels of RNA of any cancer-related genes, inflammation-related genes, and DNA-repair genes, counting any presence of tumor-specific, patient specific neoepitopes, counting any changes or ratios in RNA isotypes (splice variants) of counting any cancer-related genes and DNA-repair genes, and counting any changes in length of poly A tail of any cancer-related genes, inflammation-related genes, and DNA-repair genes.

The inventors further contemplate that each count may be weighed uniformly or biased, based on the significance of each count and then be assigned a value according to the weight of each count (e.g., each count corresponds to 1 point, some counts correspond to different scores such as 1 point, 3 points, 10 points, 100 points, etc.). Some mutations in some cancer related genes may be 'leading indicators' or triggers to activate other tumorigenesis mechanism or metastasis. Identification of such triggers may advantageously allow for early diagnosis or intervention of the cancer. Thus, for example, a mutation in a cancer-specific gene among cancer-related genes, inflammation-related genes, or DNA-repair genes may be weighed higher than other cancer-related genes or DNA-repair genes (e.g., at least 3 times, at least 5 times, at least 10 times, at least 100 times, etc.) and can be assigned to higher values accordingly. As used herein the cancer-specific gene refers any gene or mutation of the gene that is a known genetic disposition (e.g., significantly increase a susceptibility to the disease) of specific types of cancer (e.g., BRCA1 and BRCA2 for breast cancer and ovarian cancer, etc.). In another example, each gene in any cancer-related pathway or DNA-repair pathway may be differently weighed (e.g., most significant, significant, moderate, less significant, insignificant, etc.) and any mutation of a such gene that has any or no impact (e.g., adversely affect the pathway stream, etc.) on any cancer-related pathway or DNA-repair pathway may be weighed differently based on the significance of the impact. Thus, for example, gene A encoding a significant, unreplaceable protein A in a cancer pathway may be weighed heavier than another gene B encoding a redundant protein (replaceable with other proteins). Also, a nonsense mutation in gene A that results in nonfunctional protein may be weighed at least 3 times, at least 5 times, at least 10 times, at least 100 times than a silent mutation in gene A or a missense mutation which does not affect the function of protein A and can be assigned to higher values accordingly.

In some embodiments, some countings may weigh equally or differently based on the significance of each counting and then be assigned to a negative value according to the weight of each counting (e.g., each counting corresponds to −1 point, some countings correspond to different scores such as −1 point, −3 points, −10 points, −100 points, etc.). For example, upregulation of mRNA of gene C, which can compensate the loss of function of gene A, can be assigned to a negative value (e.g., −10 points) such that it can compensate the positive value of mutation of gene A (e.g., +10 points).

It is also contemplated that some countings may be differently weighed based on the degree of changes in expression level of some RNAs. For example, when the expression level of RNA "X" increases at least twice, at least 5 times, at least 10 times, at least 20 times, while other RNA expression level change is below 50% at best, then the increase of expression level of RNA "X" may be weighed at least 3 times, at least 5 times, at least 10 times, at least 100 times than other genes.

Most typically, the cancer score is compound score that is a total sum of all values assigned to all counts. In some embodiments, the cancer score can be a total sum of all values assigned to all counts (all omics data). In other embodiments, the cancer score can be a total sum of a selected number of values assigned to some counts (e.g., corresponding to specific pathways, specific types of genes, specific groups of mechanisms, etc.). Thus, the cancer score increases as more cancer-related genes or DNA-repair genes possess one or more mutations. In some embodiments, each mutation and/or change may be counted separately such that cancer scores may further increase where one or more cancer-related genes or DNA-repair genes show multiple mutations in a single gene. In other embodiments, cancer score may further increase when such multiple mutations in a single gene may further affect the function of the cancer-related genes or DNA-repair genes such that the multiple mutations drive the cells more cancer-prone, or more cancerous, or drive the cancer microenvironment more immune-resistant, and so on.

Alternatively or additionally, the cancer score can be presented as a trajectory with one or more counts as its vectors, where a few numbers of variables and/or factors dominantly govern in determination of cancer prognosis. Each of variables and/or factors can be presented as a vector, whose amplitude is corresponding to the point of each weighted counting, and the addition of those vectors provides a trajectory indicating the prognosis of the disease. Viewed form a different perspective, it should be appreciated that multiple analyses over time can be prepared for the same patient, and that changes over time (e.g., with or without treatment) may be assigned specific values that will yet again generate a time-dependent score. Such scores or changes over time may be classified and serve as leading indicator for treatment outcome, drug response, etc.

Additionally, it is also contemplated that the cancer score can be calculated with health information other than cf/ct nucleic acid data obtained from the patient's blood. For example, the health information may include expression levels/concentrations of several types of cytokines (e.g., IL-2, TNF-a, etc.) related to tumorigenesis/inflammation/ immune response against the tumor, hormone levels (e.g., estrogen, progesterone, growth hormone, etc.), blood sugar level, alanine transaminase level (for liver function), creatine level (for kidney function), blood pressure, types and quantity of tumor cell-secreted proteins (e.g., soluble ligands of immune cell receptor, etc.) or foreign antigenic proteins (e.g., for virus or bacterial infection, etc.).

The inventors contemplated that the so obtained cancer score can be used to provide a diagnosis of cancer or risk of having or developing a cancer. In some embodiments, the calculated cancer score of a patient can be compared with an average cancer score of healthy individuals to determine the difference between two scores. Preferably, when the difference between two scores is above a threshold value, the patient may be diagnosed to have a tumor, or has a high risk to have a tumor. In other embodiments, the calculated cancer score of a patient can be compared with a predetermined threshold score. The predetermined threshold score can be a predetermined score, which may vary depending on patient's ethnicity, age, gender, or other health status. In other embodiments, the predetermined threshold score can a dynamic score that can be changed based on a previous cancer score and a diagnosis or treatment performed to the patient.

The inventors also contemplate that the so obtained cancer score can be used to provide a prognosis of the cancer. For example, the cancer scores can be calculated based on omics data obtained in month 1, month 3, month 6, and month 12 after the patient got diagnosed with a first stage of lung cancer, and each cancer score can be compared with a predetermined threshold score corresponding to the month 1, 3, 6, and 12. The cancer scores are about 120% of the threshold score in month 1 and 3, and the cancer score is about 180% in month 6, and 230% of the threshold score month 12. Such progress indicates that the prognosis of the lung cancer of the patient is not optimistic if the progress is not intervened. In another example, the cancer score can be calculated by highly weighing the presence of neoepitopes that are tumor-specific and patient-specific. In this example, the cancer scores can be calculated based on omics data obtained in month 1, month 3, month 6, and month 12 after the patient got diagnosed with a first stage of lung cancer, and each cancer score is calculated by highly weighing the presence/appearance of new epitope that is tumor/tissue specific. The cancer scores are about 120% of the threshold score in month 1 and 3, and the cancer score is about 140% in month 6, and 230% of the threshold score month 12. Such progress indicates a possible metastasis of the tumor to another organ (releasing different type of neoepitope) or development of different type of tumor in the same organ (releasing different type of neoepitope).

In a further example, the cancer scores can provide an indicator for treatment options. The treatment option may be a prophylactic treatment where the compound score is below the threshold value, indicating that the patient is unlikely to have a tumor for now or at least has low risk of developing a tumor. When the cancer score is above the threshold value and a majority portion of the cancer score highly weighted was overexpression of a cancer-related gene A (e.g., over a threshold such as at least 10%, at least 20%, at least 30%, at least 50%, etc.), then the cancer score can be used to provide the treatment option that may use a drug inhibiting the activity of cancer-related gene A (e.g., a blocker of protein A, etc.). Similarly, when the cancer score is above the threshold value and a majority portion of the cancer score highly weighted was overexpression of a gene encoding a receptor of an immune cell or a ligand of the receptor, then the cancer score can be used to provide the immunotherapy using the receptor or ligand of the immune cells. Also, when the cancer score is above the threshold value and a majority portion of the cancer score highly weighted was overexpression of a specific neoepitope, then the cancer score can be used to provide the immunotherapy using the neoepitope as a bait or a surgery/a radiation therapy to physically remove local tumors. Also such cancer scores may be an indicative of likelihood of success for the treatment option. However, if the portion of the cancer score highly weighted was overexpression of a cancer-related gene A is below the threshold, then the treatment option using a drug inhibiting the activity of cancer-related gene A may be predicted less effective.

Consequently, the patient can be treated with at least one of the treatment options based on the patient's cancer (compound) score. For example, above the threshold value and a majority portion of the cancer score highly weighted was overexpression of a specific neoepitope, the treatment option can be selected to include a recombinant virus (or yeast or bacteria) comprising a nucleic acid encoding the specific neoepitope. Then, the recombinant virus can be administered to the patient in a dose and schedule effective to treat the tumor and/or effective to reduce the cancer score of the patient for at least 10%, at least 20%, at least 30%, at least in 2 weeks, at least in 4 weeks, at least in 8 weeks, at least in 12 weeks after the administration or a series of administrations.

It is also contemplated that the patient's cancer score can be compared with one or more other patients having same type of cancer and having a treatment history to provide a treatment option and predicted outcome. For example, where other patients' history indicates that the drug treatment is effective only when the cancer score is below 200 (as absolute score), or less than 180% of the healthy individual's score, and the patient's cancer score has been increasing from 140 to 160 for the last 2 weeks, a recommendation to proceed with drug treatment no later than 2 weeks can be provided based on the other patients' history and cancer scores.

The calculated cancer score can also be an indicator of an effectiveness of a cancer treatment, especially when the omics data includes information of at least one or more genes encoding a target/indicator of the cancer treatment. For example, cancer scores can be calculated based on omics data obtained before the cancer treatment, 7 days after, 2 weeks, 1 month, and 6 months of the cancer treatment. The cancer score of 7 days after the treatment is 80% of the cancer score before the treatment, and the cancer score of 2 weeks and 1 month after the treatment is 50% of the cancer score before the treatment, and the cancer score of 6 months after the treatment is 150% of the cancer score before the treatment. Such progress indicates that the treatment was effective at least for a short term (e.g., up to 1 month), yet the effectiveness is decreased over time and may not effective at all in 6 months after the treatment. In some embodiments, the cancer scores before and after treatment can be compared with a predetermined threshold value to determine the effectiveness of the treatment. For example, if the cancer score is 200 before the treatment and 130 after the treatment where the threshold cancer score is 100, then the treatment can be determined "effective" as the cancer score drops below the threshold after the treatment. However, if the cancer score is 200 before the treatment and 160 after the treatment where the threshold cancer score is 150, then the treatment can be determined "not effective" as the cancer score stays above the threshold after the treatment even though the absolute value of the cancer score is decreased. Consequently, the inventors further contemplate that the patient continues with administering the treatment option (e.g., immune therapy, etc.) when the treatment can be determined "effective", when the cancer score after the treatment is lower than the predetermined threshold, when the cancer score after the treatment is at most 5%, at most 10% higher than the predetermined threshold, or when the cancer score after the treatment is at least 5%, at least 10%, at least 15% lower than the predetermined threshold. s The inventors also contemplate that the effectives of some cancer treatments can be determined by analyzing omics data including foreign DNA/RNA originated from a carrier of the immune therapy (e.g., virus, bacteria, yeast, etc.). For example, where the virus is a carrier to deliver a recombinant nucleic acid encoding recombinant killer activation receptor (KAR), the level of cell free DNA/RNA of recombinant KAR in the patient blood can be an indicator of an effectiveness of infection of the virus.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A method of analyzing omics data and treating a patient having a cancer, the method comprising:
   obtaining blood from the patient having or suspected to have the cancer;
   obtaining, from the blood, omics data for a plurality of cancer-related genes, wherein the omics data comprise at least one of DNA sequence data, RNA sequence data, and RNA expression level data; providing an omics record computer system that includes at least one processor and at least one computer readable memory coupled to the processor and configured to digitally store the omics data for the plurality of cancer-related genes in the at least one memory;
   calculating, in silico, a digital score from the digital omics data, wherein the digital score is calculated in silico by the sum of (i) counting the number of mutations of cancer-related genes, inflammation-related genes, and DNA-repair genes, (ii) counting changes in methylation or modifications in DNA of cancer-related genes and DNA-repair genes, (iii) counting upregulation or downregulation in expression levels of RNA of cancer-related genes, inflammation-related genes, and DNA-repair genes, (iv) counting the number of tumor- and patient-specific neoepitopes, (v) counting splice variants of cancer-related genes and DNA-repair genes, and (vi) counting changes in length of poly A tail of any cancer-related genes, inflammation-related genes, and DNA-repair genes;
   associating the digital score with at least one of a health status, an omics error status, a cancer prognosis, a therapeutic recommendation, an effectiveness of a treatment; and
   upon the digital score reaching a threshold value and a majority portion of the digital score is highly weighted as an overexpression of a specific neoepitope;
   generating a personalized treatment option for the patient, wherein the personalized treatment option comprises a recombinant nucleic acid encoding one or more tumor- and patient-specific neoepitopes; and
   treating the cancer by administering the personalized treatment option to the patient.

2. The method of claim 1, wherein the plurality of cancer-related genes comprises at least one of a cancer-related gene, a cancer-specific gene, a DNA-repair gene, a neoepitope, and a gene not associated with a disease.

3. The method of claim 1, wherein the DNA sequence data is selected from the group consisting of mutation data, copy number data duplication, loss of heterozygosity data, and epigenetic status.

4. The method of claim 1, wherein the RNA sequence data is selected from the group consisting of mRNA sequence data and splice variant data.

5. The method of claim 1, wherein the RNA expression level data is selected from the group consisting of a quantity of RNA transcript and a quantity of a small noncoding RNA.

6. The method of claim 1, wherein DNA sequence data is obtained from circulating free DNA.

7. The method of claim 1, wherein the RNA sequence data is obtained from the group consisting of circulating tumor RNA and circulating free RNA.

8. The method of claim 3, wherein the plurality of cancer-related genes includes a cancer-specific gene, and the digital score is calculated based on a presence or an absence of a mutation in the cancer-specific gene.

9. The method of claim 8, wherein the presence of the mutation in the cancer-specific gene weighs more than the presence of the mutation in the cancer-related genes other than the cancer-specific gene.

10. A method of determining prognosis of a cancer of a patient and treating the patient having the cancer, the method comprising:
    obtaining blood from the patient having the cancer;
    obtaining from the blood omics data of the cancer patient for a plurality of cancer genes, wherein the omics data comprise at least one of DNA sequence data, RNA sequence data, and RNA expression level;
    providing an omics record computer system that includes at least one processor and at least one computer readable memory coupled to the processor and configured to digitally store the omics data for the plurality of cancer-related genes in the at least one memory;
    analyzing, in silico, the digital omics data to obtain a digital cancer prognosis score, wherein the digital cancer prognosis score is calculated in silico by the sum of (i) counting the number of mutations of cancer-related genes, inflammation-related genes, and DNA-repair genes, (ii) counting changes in methylation or modifications in DNA of cancer-related genes and DNA-repair genes, (iii) counting upregulation or downregulation in expression levels of RNA of cancer-related genes, inflammation-related genes, and DNA-repair genes, (iv) counting the number of tumor-specific, patient specific neoepitopes, (v) counting splice variants of cancer-related genes and DNA-repair genes, and (vi) counting changes in length of poly A tail of any cancer-related genes, inflammation-related genes, and DNA-repair genes;

providing the prognosis of the cancer based on the digital cancer prognosis score; and upon the digital cancer prognosis score reaching a threshold value and a majority portion of the digital cancer prognosis score is highly weighted as an overexpression of a specific neoepitope:

generating a personalized treatment option for the patient, wherein the personalized treatment option comprises a recombinant nucleic acid encoding one or more tumor- and patient-specific neoepitopes; and treating the cancer by administering the personalized treatment option to the patient.

11. The method of claim 10, wherein the plurality of cancer-related genes comprises at least one of a cancer-related gene, a cancer-specific gene, a DNA-repair gene, a neoepitope, and a gene not associated with a disease.

12. The method of claim 10, wherein the DNA sequence data are selected from the group consisting of mutation data, copy number data duplication, loss of heterozygosity data, and epigenetic status.

13. The method of claim 10, wherein the RNA sequence data are selected from the group consisting of mRNA sequence data and splice variant data.

14. The method of claim 10, wherein the RNA expression level data are selected from the group consisting of a quantity of RNA transcript and a quantity of a small non-coding RNA.

15. The method of claim 10, wherein DNA sequence data are obtained from circulating free DNA.

16. The method of claim 10, wherein the RNA sequence data are obtained from the group consisting of circulating tumor RNA and circulating free RNA.

17. The method of claim 12, wherein the plurality of cancer-related genes includes a cancer-specific gene, and the digital cancer prognosis score is calculated based on a presence or an absence of a mutation in the cancer-specific gene.

18. A method of predicting an outcome of a treatment for a cancer patient, the method comprising:

obtaining blood from a patient having a cancer; obtaining from the blood omics data of the cancer patient for a plurality of cancer genes, wherein the omics data comprise at least one of DNA sequence data, RNA sequence data, and RNA expression level;

providing an omics record computer system that includes at least one processor and at least one computer readable memory coupled to the processor and configured to digitally store the omics data for the plurality of cancer-related genes in the at least one memory;

analyzing, in silico, the omics data to generate a digital cancer gene score, wherein the digital cancer gene score is calculated in silico by the sum of (i) counting the number of mutations of cancer-related genes, inflammation-related genes, and DNA-repair genes, (ii) counting changes in methylation or modifications in DNA of cancer-related genes and DNA-repair genes, (iii) counting upregulation or downregulation in expression levels of RNA of cancer-related genes, inflammation-related genes, and DNA-repair genes, (iv) counting the number of tumor-specific, patient specific neoepitopes, (v) counting splice variants of cancer-related genes and DNA-repair genes, and (vi) counting changes in length of poly A tail of any cancer-related genes, inflammation-related genes, and DNA-repair genes; and providing, in silico, a predicted outcome of the treatment based on the digital cancer gene score; and upon the digital cancer gene score reaching a threshold value and a majority portion of the digital cancer gene score is highly weighted as an overexpression of a specific neoepitope:

generating a personalized treatment option for the patient, wherein the personalized treatment option comprises a recombinant nucleic acid encoding one or more tumor- and patient-specific neoepitopes; and treating the cancer by administering the personalized treatment option to the patient.

\* \* \* \* \*